United States Patent [19]

Sohda et al.

[11] Patent Number: 5,614,544
[45] Date of Patent: Mar. 25, 1997

[54] OXAZOLIDINEDIONE DERIVATIVES AND THEIR USE

[75] Inventors: Takashi Sohda, Takatsuki; Hitoshi Ikeda, Higashiosaka; Yu Momose, Takarazuka, all of Japan

[73] Assignee: Takeda Chemical Industries, Ltd., Osaka, Japan

[21] Appl. No.: 303,209

[22] Filed: Sep. 8, 1994

[30] Foreign Application Priority Data

Sep. 14, 1993 [JP] Japan .................................. 5-227679
Jul. 29, 1994 [JP] Japan .................................. 6-178683

[51] Int. Cl.$^6$ .................................................. A61K 31/42
[52] U.S. Cl. .......................... 514/376; 548/226; 548/217; 548/236; 548/117; 548/187; 548/186; 544/238
[58] Field of Search ............................. 514/376; 548/226

[56] References Cited

U.S. PATENT DOCUMENTS

| | | | |
|---|---|---|---|
| 4,430,337 | 2/1984 | Holland | 514/376 |
| 4,448,971 | 5/1984 | Schnur | 548/226 |
| 5,334,606 | 8/1994 | McLeod | 514/376 |
| 5,498,621 | 3/1996 | Dow et al. | 514/376 |

FOREIGN PATENT DOCUMENTS

| | | |
|---|---|---|
| 332332 | 9/1989 | European Pat. Off. . |
| 0332331 | 9/1989 | European Pat. Off. . |
| 0428312 | 5/1991 | European Pat. Off. . |
| 1-272573 | 10/1989 | Japan . |
| 1-272574 | 10/1989 | Japan . |
| WO92/02520 | 2/1992 | WIPO . |

OTHER PUBLICATIONS

Hulin, Jour Med Chem vol. 35, 1853–1864 (1992).
Dow et al., J. Med. Chem., vol. 34, No. 5, May 1991, pp. 1538–1544 Washington U.S.A.

*Primary Examiner*—Donald G. Daus
*Attorney, Agent, or Firm*—Wenderoth, Lind & Ponack

[57] ABSTRACT

[Object]

To provide a new 2,4-oxazolidinedione derivative possessing excellent hypoglycemic and hypolipidemic activities.

[Constituent]

A 2,4-oxazolidinedione derivative represented by the general formula:

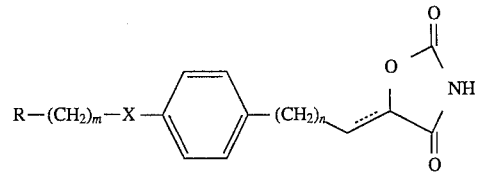

wherein X represents —$CH_2$—, —$C(=O)$—, —$CH(OH)$—, —$C(=NOH)$— or —$CH=CH$—; R represents a hydrocarbon residue or heterocyclic group which may be substituted; n represents an integer from 0 to 5, and m represents an integer from 1 to 3; ....... represents a single or double bond; provided that n is an integer from 1 to 5 when X is —$C(=O)$—, or a pharmacologically acceptable salt thereof.

[Drawings selected]

None

10 Claims, No Drawings

OXAZOLIDINEDIONE DERIVATIVES AND THEIR USE

The present invention relates to a new oxazolidinedione derivative possessing hypoglycemic and hypolipidemic activities and a therapeutic agent for diabetes mellitus containing it, which are used in the pharmaceutical field.

Traditionally, various biguanide compounds and sulfonylurea compounds have been used to treat diabetes mellitus. However, biguanide compounds are now hardly used, since they cause lactic acid acidosis; sulfonylurea compounds often cause severe hypoglycemia, necessitating careful use, although they possess potent hypoglycemic activity. Various oxazolidinedione derivatives are known to possess hypoglycemic activity without such drawbacks.

Japanese Patent Unexamined Publication No. 170478/1991 (corresponding to EP-A-428312, published May 22, 1991 in the English language) discloses a hypoglycemic compound represented by the formula:

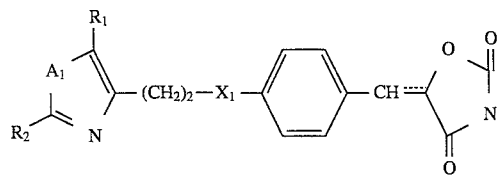

wherein $X_1$ represents O or C=O. WO92/02520 discloses a hypoglycemic compound represented by the formula:

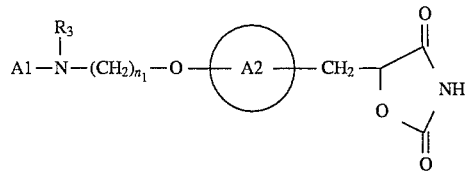

wherein A2 represents a optionally substituted benzene. Japanese Patent EXAMINED Publication NO. 30993/1987(corresponding to U.S. Pat. No. 4,430,337) discloses a hypoglycemic 2,4oxazolidinedione derivative represented by the formula:

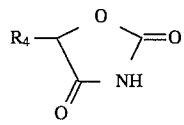

wherein $R_4$ represents an alicyclic hydrocarbon having a substituent.

The present inventors extensively investigated the number of carbon atoms between the oxazolidinedione ring and benzene ring in a 2,4-oxazolidinedione derivative and the 4-position substituent on the benzene ring, and discovered a new derivative possessing excellent hypoglycemic and hypolipidemic activities.

Accordingly, the present invention relates to:

(1) a 2,4oxazolidinedione derivative represented by the general formula:

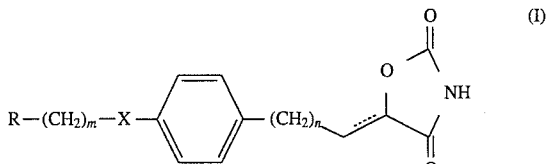

wherein X represents —$CH_2$—, —C(=O)—, —CH(OH)—, —C(=NOH)— or —CH=CH—; R represents a hydrocarbon residue or heterocyclic group which may be substituted; n represents an integer from 0 to 5, and m represents an integer from 1 to 3; ....... represents a single or double bond; provided that n is an integer from 1 to 5 when X is —C(=O)—, or a salt thereof, and (2) a pharmaceutical composition containing as an active ingredient a 2,4—oxazolidinedione derivative represented by general formula (I), or a pharmaceutically acceptable salt thereof.

With respect to general formula (I) above, a single bond represented by ....... corresponds to a compound wherein —$(CH_2)_n$— and the oxazolidinedione ring are bound together via —$CH_2$—, and a double bond represented by ....... corresponds to a compound wherein —$(CH_2)_n$—CH= is bound with the oxazolidinedione ring. The compound (I) wherein ....... is a double bond may be in (E)-form or in (Z)-form.

Of the compounds represented by general formula (I) above, those wherein n is an integer from 1 to 5 and those wherein m is 1 or 2 are preferred, with greater preference given to compounds wherein m is 2 and n is 1 or 2 and compounds wherein m is 1 and n is 2. X is preferably —$CH_2$—, —CH(OH), —C(=NOH)— or —CH=CH—; in this case, it is preferable that n be 0 and m be 1 or 2. More preferably, X is —$CH_2$— or —CH=CH—.

With respect to general formula (I) above, the hydrocarbon residue in the hydrocarbon residue for R which may be substituted is exemplified by aliphatic hydrocarbon residues, alicyclic hydrocarbon residues, alicyclic-aliphatic hydrocarbon residues, aromato-aliphatic hydrocarbon residues, aromatic hydrocarbon residues and aromatic heterocyclic-aliphatic hydrocarbon residues. Such aliphatic hydrocarbon residues include aliphatic hydrocarbon residues having 8 or fewer carbon atoms, e.g., saturated aliphatic hydrocarbon residues having 1 to 8 carbon atoms such as methyl, ethyl, propyl, isopropyl, butyl, isobutyl, sec-butyl, t-butyl, pentyl, isopentyl, neopentyl, t-pentyl, hexyl, isohexyl, heptyl and octyl, and unsaturated aliphatic hydrocarbon residues having 2 to 8 carbon atoms such as ethenyl, 1-propenyl, 2-propenyl, 1-butenyl, 2-butenyl, 3-butenyl, 2-methyl-1-propenyl, 1-pentenyl, 2-pentenyl, 3-pentenyl, 4-pentenyl, 3-methyl-2-butenyl, 1-hexenyl, 3-hexenyl, 2,4-hexadienyl, 5-hexenyl, 1-heptenyl, 1-octenyl, ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 3-hexynyl, 2,4-hexadiynyl, 5-hexynyl, 1-heptynyl and 1-octynyl. Such alicyclic hydrocarbon residues include alicyclic hydrocarbon residues having 3 to 7 carbon atoms, e.g., saturated alicyclic hydrocarbon residues having 3 to 7 carbon atoms such as cyclopropyl, cyclobutyl, cyclopentyl, cyclohexyl and cycloheptyl, and unsaturated alicyclic hydrocarbon residues having 5 to 7 carbon atoms such as 1-cyclopentenyl, 2-cyclopentenyl, 3-cyclopentenyl, 1-cyclohexenyl, 2-cyclohexenyl, 3-cyclohexenyl, 1-cycloheptenyl, 2-cycloheptenyl, 3-cycloheptenyl and 2,4-cycloheptadienyl. Such alicyclic-aliphatic hydrocarbon residues include hydrocarbon residues having 4 to 9 carbon atoms as resulting from binding of one of the above-mentioned alicyclic hydrocarbon residues and one of the above-mentioned aliphatic hydrocarbon residues, such as cyclopropylmethyl, cyclopropylethyl, cyclobutylmethyl, cyclopentylmethyl, 2-cyclopentenylmethyl, 3-cyclopentenylmethyl, cyclohexylmethyl, 2-cyclohexenylmethyl, 3-cyclohexenylmethyl, cyclohexylethyl, cyclohexylpropyl, cycloheptylmethyl and cycloheptylethyl. Such aromato-aliphatic hydrocarbon residues include phenylalkyls having 7 to 9 carbon atoms such as benzyl, phenethyl, 1-phenylethyl, 3-phenylpropyl, 2-phenylpropyl and 1-phenylpropyl, and naphthylalkyls having 11 to 13 carbon atoms such as α-naphthylmethyl, α-naphthylethyl, β-naphthylmethyl and β-naphthylethyl. Such aromatic hydrocarbon residues include phenyl and naphthyl (α-naphthyl, β-naphthyl). Such aromatic heterocyclic-aliphatic hydrocarbon residues include hydrocarbon residues resulting from binding of one of the following heterocyclic groups and one of the aliphatic hydrocarbon residues.

With respect to general formula (I) above, the heterocyclic group in the heterocyclic group for R which may be substituted is exemplified by 5- to 7-membered heterocyclic groups containing 1 atom of sulfur, nitrogen or oxygen, 5- or 6-membered heterocyclic groups containing 2 to 4 atoms of nitrogen, and 5- or 6-membered heterocyclic groups containing 1 or 2 atoms of nitrogen and 1 atom of sulfur or oxygen; these heterocyclic groups may condense with a 6-membered ring containing 2 or fewer atoms of nitrogen, a benzene ring or a 5-membered ring containing 1 atom of sulfur. Example heterocyclic groups include 2-pyridyl, 3-pyridyl, 4-pyridyl, 2-pyrimidinyl, 4-pyrimidinyl, 5-pyrimidinyl, 6-pyrimidinyl, 3-pyridazinyl, 4-pyridazinyl, 2-pyrazinyl, 2-pyrrolyl, 3-pyrrolyl, 2-imidazolyl, 4-imidazolyl, 5-imidazolyl, 3-pyrazolyl, 4-pyrazolyl, isothiazolyl, isoxazolyl, 2-thiazolyl, 4-thiazolyl, 5-thiazolyl, 2-oxazolyl, 4-oxazolyl, 5-oxazolyl, 1,2,4-triazol-3-yl, 1,2,3-triazol 4-yl, tetrazol-5-yl, benzimidazol-2-yl, indol-3-yl, benzopyrazol-3-yl, 1H-pyrrolo[2,3-]pyrazin-2-yl, 1H-pyrrolo[2,3-b]pyridin-6-yl, 1H-imidazo[4,5b]pyridin-2-yl, 1H-imidazo[4,5-c]pyridin-2-yl and 1H-imidazo[4,5-b]pyrazin-2-yl.

With respect to general formula (I) above, the hydrocarbon residue or heterocyclic group for R may have 1 to 3 substituents at any positions on the ring thereof. Such substituents include aliphatic chain hydrocarbon groups, alicyclic hydrocarbon groups, aryl groups, aromatic heterocyclic groups, nonaromatic heterocyclic groups, halogen atoms, nitro groups, amino groups which may be substituted, acyl groups which may be substituted, hydroxyl groups which may be substituted, thiol groups which may be substituted, and carboxyl groups which may be esterified. Such aliphatic chain hydrocarbon groups include linear or branched aliphatic hydrocarbon groups such as alkyl groups, preferably those having 1 to 10 carbon atoms, alkenyl groups, preferably those having 2 to 10 carbon atoms, and alkynyl groups. Preferable alkyl groups include methyl, ethyl, propyl, isopropyl, butyl, isobutyl, sec-butyl, tert-butyl, pentyl, isopentyl, neopentyl, tert-pentyl, 1-ethylpropyl, hexyl, isohexyl, 1,1-dimethylbutyl, 2,2-dimethylbutyl, 3,3-dimethylbutyl, 2ethylbutyl, heptyl, octyl, nonyl and decyl. Preferable alkenyl groups include vinyl, allyl, isopropenyl, 1-propenyl, 2-methyl-1-propenyl, 1-butenyl, 2butenyl, 3-butenyl, 2-ethyl-1-butenyl, 3-methyl-2-butenyl,. 1-pentenyl, 2-pentenyl, 3-pentenyl, 4-pentenyl, 4-methyl-3-pentenyl, 1-hexenyl, 2-hexenyl, 3-hexenyl, 4-hexenyl and 5-hexenyl. Preferable alkynyl groups include ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4hexynyl and 5-hexynyl. Such alicyclic hydrocarbon groups include saturated or unsaturated alicyclic hydrocarbon groups such as cycloalkyl groups, cycloalkenyl groups and cycloalkadienyl groups. Preferable cycloalkyl groups include cyclopropyl, cyclobutyl, cyclopentyl, cyclohexyl, cycloheptyl, cyclooctyl, bicyclo[2.2.1]heptyl, bicyclo [2.2.2]octyl, bicyclo[3.2.1]octyl, bicyclo[3.2.2]nonyl, bicyclo[3.3.1]nonyl, bicyclo[4.2.1]nonyl and bicyclo[4.3.1] decyl. Preferable cycloalkenyl groups include 2-cyclopenten-1-yl, 3-cyclopenten-1-yl, 2-cyclohexen-1-yl and 3-cyclohexen-1-yl. Preferable cycloalkadienyl groups include 2,4-cyclopentadien-1-yl, 2,4-cyclohexadien-1-yl and 2,5-cyclohexadien-1-yl. The aryl group is a monocyclic or condensed polycyclic aromatic hydrocarbon group. Preferable aryl groups include phenyl, naphthyl, anthryl, phenanthryl and acenaphthylenyl, with preference given to phenyl, 1-naphthyl, 2-naphthyl etc. Preferable aromatic heterocyclic groups include aromatic monocyclic heterocyclic groups such as furyl, thienyl, pyrrolyl, oxazolyl, isoxazolyl, thiazolyl, isothiazolyl, imidazolyl, pyrazolyl, 1,2,3-oxadiazolyl, 1,2,4-oxadiazolyl, 1,3,4-oxadiazolyl, furazanyl, 1,2,3-thiadiazolyl, 1,2,4-thiadiazolyl, 1,3,4-thiadiazolyl, 1,2,3-triazolyl, 1,2,4-triazolyl, tetrazolyl, pyridyl, pyridazinyl, pyrimidinyl, pyrazinyl and triazinyl, and aromatic condensed heterocyclic groups such as benzofuranyl, isobenzofuranyl, benzo[b]thienyl, indolyl, isoindolyl, 1H-indazolyl, benzimidazolyl, benzoxazolyl, 1,2-benzisoxazolyl, benzothiazolyl, 1,2-benzisothiazolyl, 1H-benzotriazolyl, quinolyl, isoquinolyl, cinnolinyl, quinazolinyl, quinoxalinyl, phthalazinyl, naphthyridinyl, purinyl, pteridinyl, carbazolyl, α-carbolinyl, β-carbolinyl, γ-carbolinyl, acridinyl, phenoxazinyl, phenothiazinyl, phenazinyl, phenoxthinyl, thianthrenyl, phenanthridinyl, phenanthrolinyl, indolizinyl, pyrrolo[1,2-b]pyridazinyl, pyrazolo[1,5-a]pyridyl, imidazo[1,2-a] pyridyl, imidazo[1,5-a]pyridyl, imidazo[1,2-b]pyridazinyl, imidazo[1,2-a]pyrimidinyl, 1,2,4-triazolo[4,3a]pyridyl and 1,2,4-triazolo[4,3-b]pyridazinyl. Preferable non-aromatic heterocyclic groups include oxilanyl, azetidinyl, oxetanyl, thietanyl, pyrrolidinyl, tetrahydrofuryl, thiolanyl, piperidyl, tetrahydropyranyl, morpholinyl, thiomorpholinyl and piperazinyl. Such halogens include fluorine, chlorine, bromine and iodine, with preference given to fluorine and chlorine. Said hydroxyl group which may be substituted is exemplified by the hydroxyl group and groups resulting from substitution of the hydroxyl group by an appropriate substituent, particularly one commonly used as a hydroxyl-protecting group, such as alkoxy groups, alkenyloxy groups, aralkyloxy groups, acyloxy groups and aryloxy groups. Such alkoxy groups include alkoxy groups having 1 to 10 carbon atoms (e.g., methoxy, ethoxy, propoxy, isopropoxy, butoxy, isobutoxy, sec-butoxy, tert-butoxy, pentyloxy, isopentyloxy, neopentyloxy, hexyloxy, heptyloxy, nonyloxy, cyclobutoxy, cyclopentyloxy, cyclohexyloxy). Such alkenyloxy groups include alkenyloxy groups having 1 to 10 carbon atoms such as allyloxy, crotyloxy, 2-pentenyloxy, 3-hexenyloxy, 2-cyclopentenylmethoxy and 2-cyclohexenylmethoxy. Such aralkyloxy groups include phenyl—$C_{1-4}$ alkyloxy groups (e.g., benzyloxy, phenethyloxy). Such acyloxy groups include alkanoyloxy groups having 2 to 4 carbon atoms (e.g., acetyloxy, propionyloxy, n-butyryloxy, iso-butyryloxy). Such aryloxy groups include phenoxy and 4-chlorophenoxy. Said thiol group which may be substituted is exemplified by the thiol group as such and groups resulting from substitution of the thiol group by an appropriate substituent, particularly one commonly used as a thiol-protecting group, such as alkylthio groups, aralkylthio groups and acylthio groups. Preferable alkylthio groups include alkylthio groups having 1 to 10 carbon atoms (e.g., methylthio, ethylthio, propylthio, isopropylthio, butylthio, isobutylthio, sec-butylthio, tert-butylthio, pentylthio, isopentylthio, neopentylthio, hexylthio, heptylthio, nonylthio, cyclobutylthio, cyclopentylthio, cyclohexylthio). Aralkylthio groups include phenyl-$C_{1-4}$ alkylthio groups (e.g., benzylthio, phenethylthio). Preferable acylthio groups include alkanoylthio groups having 2 to 4 carbon atoms (e.g., acetylthio, propionylthio, n-butyrylthio, iso-butyrylthio). Said amino group which may be substituted is exemplified by groups resulting from substitution of the amino group (—$NH_2$ group) by 1 or 2 alkyl groups having 1 to 10 carbon atoms, alkenyl groups having 1 to 10 carbon atoms, aromatic groups or acyl group having 2 to 10 carbon atoms (e.g., methylamino, dimethylamino, ethylamino, diethylamino, dibutylamino, diallylamino, cyclohexylamino, phenylamino, N-methyl-N-phenylamino, acetylamino, propionylamino, benzoylamino, etc.). Said acyl group which may be substituted is exemplified by formyl and groups resulting from binding of the carbonyl group with an alkyl group having 1 to 10 carbon atoms, an alkenyl group having 1 to 10 carbon atoms or an aromatic group (e.g., acetyl, propionyl, butyryl, isobutyryl, valeryl, isovaleryl, pivaloyl, hexanoyl, heptanoyl, octanoyl, cyclobutanecarbonyl, cyclopentanecarbonyl, cyclohexanecarbonyl, cycloheptanecarbonyl, crotonyl, 2-cyclohexenecarbonyl, benzoyl, nicotinoyl). Said carboxyl group which may be esterified is exemplified by alkoxycarbonyl groups (e.g., alkoxycarbonyl groups having 2 to 5 carbon atoms such as methoxycarbonyl, ethoxycarbonyl, propoxycarbonyl, butoxycarbonyl), aralkyloxycarbonyl groups (e.g., benzyloxycarbonyl) and aryloxycarbonyl groups (e.g., phenoxycarbonyl, p-tolyloxycarbonyl).

With respect to general formula (I) above, the substituent on the hydrocarbon residue or heterocyclic group for R may have 1 or more, preferably 1 to 3 appropriate substituents, provided that it is an alicyclic hydrocarbon residue, an aryl group or an aromatic heterocyclic group. Such substituents include lower alkyl groups, lower alkenyl groups, lower alkynyl groups, cycloalkyl groups, aryl groups, aromatic heterocyclic groups, non-aromatic heterocyclic groups, aralkyl groups, amino groups, N-monosubstituted amino groups, N,N-disubstituted amino groups, amidino groups, acyl groups, carbamoyl groups, N-monosubstituted carbamoyl groups, N,N-disubstituted carbamoyl groups, sulfamoyl groups, N-monosubstituted sulfamoyl groups, N,N-disubstituted sulfamoyl groups, carboxyl groups, lower alkoxycarbonyl groups, hydroxyl groups, lower alkoxy groups, lower alkenyloxy groups, cycloalkyloxy groups, aralkyloxy groups, aryloxy groups, mercapto groups, lower alkylthio groups, aralkylthio groups, arylthio groups, sulfo groups, cyano groups, azide groups, nitro groups, nitroso groups and halogens. Such substituents are exemplified by the same substituents as those on the ring of the hydrocarbon residue or heterocyclic group for R above.

The salt of desired compound (I) of the present invention is preferably a pharmaceutically acceptable salt. Such salts include salts with inorganic bases, salts with organic bases, salts with inorganic acids, salts with organic acids and salts with basic or acidic amino acids. Preferable salts with inorganic bases include alkali metal salts such as sodium salt and potassium salt, alkaline earth metal salts such as calcium salt and magnesium salt, aluminum salt and ammonium salt. Preferable salts with organic bases include salts with trimethylamine, triethylamine, pyridine, picoline, ethanolamine, diethanolamine, triethanolamine, dicyclohexylamine and N,N'-dibenzylethylenediamine. Preferable salts with inorganic acids include salts with hydrochloric acid, hydrobromic acid, nitric acid, sulfuric acid and phosphoric acid. Preferable salts with organic acids include salts with formic acid, acetic acid, trifluoroacetic acid, fumaric acid, oxalic acid, tartaric acid, maleic acid, citric acid, succinic acid, malic acid, methanesulfonic acid, benzenesulfonic acid and p-toluenesulfonic acid. Preferable salts with basic amino acids include salts with arginine, lysine and ornithine. Preferable salts with acidic amino acids include salts with aspartic acid and glutamic acid.

Possessing hypoglycemic and hypolipidemic activity with low toxicity, desired compound (I) of the present invention or a pharmacologically acceptable salt thereof can be used, as such or in a mixture with known pharmacologically acceptable carriers, excipients, fillers and other additives, as a therapeutic agent for diabetes mellitus or hyperlipidemia in mammals including humans.

Desired compound (I) of the present invention or a pharmacologically acceptable salt thereof is characterized by low toxicity; for example, oral administration of the compound of Example 2 at a daily dose of 11.8 mg/kg or the compound of Example 5 at a daily dose of 7.5 mg/kg for 4 days in mice caused no changes in body weight or liver weight, in comparison with control animals. And, oral administration of the compound obtained in Example 13 at a dose of 500 mg/kg to mice killed no test animals.

As for method of administration, desired compound (I) of the present invention or a pharmacologically acceptable salt thereof is normally administered orally in the form of tablets, capsules (including soft capsules and microcapsules), powders, granules etc., and can also be administered non-orally in the form of injections, suppositories, pellets etc., in some cases. Daily oral dose for adults is 0.05 to 10 mg/kg; it is desirable to administer this dose in 1 to 3 portions daily.

Compound (I) of the present invention or a pharmacologically acceptable salt thereof can be administered orally or non-orally in the form of solid preparations such as tablets, capsules, granules and powders or liquid preparations such as syrups and injections, in a mixture with a pharmaceutically acceptable carrier.

Pharmaceutically acceptable carriers are various organic or inorganic carrier materials commonly used to prepare pharmaceutical preparations, which are formulated as excipients, lubricants, binders and disintegrating agents in solid preparations, or as solvents, dissolution aids, suspending agents, isotonizing agents, buffers and analgesics in liquid preparations. Also, preparation additives such as preservatives, antioxidants, coloring agents and sweeteners may be used as necessary. Preferable excipients include lactose, sucrose, D-mannitol, starch, crystalline cellulose and light silicic anhydride. Preferable lubricants include magnesium stearate, calcium stearate, talc and colloidal silica. Preferable binders include crystalline cellulose, sucrose, D-mannitol, dextrin, hydroxypropyl cellulose, hydroxypropylmethyl cellulose and polyvinylpyrrolidone. Preferable disintegrating agents include starch, carboxymethyl cellulose, carboxymethyl cellulose calcium, cross carmellose sodium and carboxymethyl starch sodium. Preferable solvents include water for injection, alcohol, propylene glycol, macrogol, sesame oil and corn oil. Preferable dissolution aids include polyethylene glycol, propylene glycol, D-mannitol, benzyl benzoate, ethanol, tris-aminomethane, cholesterol, triethanolamine, sodium carbonate and sodium citrate. Preferable suspending agents include surfactants such as stearyltriethanolamine, sodium lauryl sulfate, laurylaminopropionic acid, lecithin, benzalkonium chloride, benzethonium chloride and glycerol monostearate, and hydrophilic polymers such as polyvinyl alcohol, polyvinylpyrrolidone, carboxymethyl cellulose sodium, methyl cellulose, hydroxymethyl cellulose, hydroxyethyl cellulose and hydroxypropyl cellulose. Preferable isotonizing agents include sodium chloride, glycerol and D-mannitol. Preferable buffers include phosphate, acetate, carbonate and citrate buffers. Preferable analgesics include benzyl alcohol. Preferable preservatives include p-oxybenzoates, chlorobutanol, benzyl alcohol, phenethyl alcohol, dehydroacetic acid and sorbic acid. Preferable antioxidants include sulfites and ascorbic acid.

Production methods for desired compound (I) of the present invention are described in detail below.

Method A

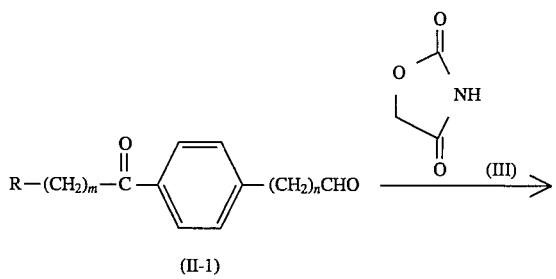

(II-1)

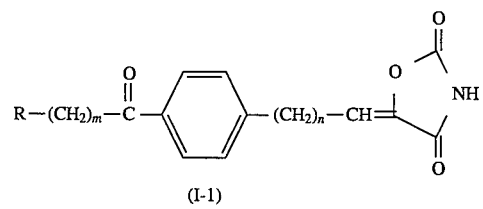

(I-1)

wherein the symbols have the same definitions as above.

Compound (I-1) is produced by condensation of compound (II-1) and 2,4oxazolidinedione (III). Condensation of compound (II-1) and 2,4oxazolidinedione (III) is carried out in a solvent in the presence of a base. The solvent is exemplified by alcohols such as methanol, ethanol, propanol, isopropanol and 2-methoxyethanol, aromatic hydrocarbons such as benzene, toluene and xylene, ethers such as ethyl ether, isopropyl ether, dioxane and tetrahydrofuran, N,N-dimethylformamide, dimethyl sulfoxide and acetic acid. The base is exemplified by sodium alkoxides (e.g., sodium methoxide, sodium ethoxide), potassium carbonate, sodium carbonate, sodium hydride, sodium acetate, and secondary amines such as piperidine, piperazine, pyrrolidine, morpholine, diethylamine and diisopropylamine. The amount of 2,4-oxazolidinedione (III) used is 1 to 10 mol equivalents, preferably 1 to 5 mol equivalents relative to compound (II-1). The amount of base used is 0.01 to 5 mol equivalents, preferably 0.05 to 2 mol equivalents relative to compound (II-1). This reaction is normally carried out at 0° to 150° C., preferably 20° to 100° C. for 0.5 to 30 hours. The compound (I-1) produced in this method may be in (E)-form or (Z)-form at the double bond attached to the 5-position of the oxazolidinedione ring.

Method B (I-1) 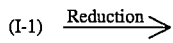

-continued
Method B

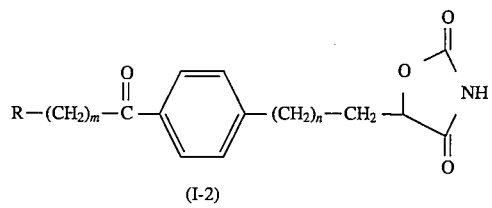

(I-2)

wherein the symbols have the same definitions as above.

Compound (I-2) is produced by subjecting compound (I-1) to a reduction reaction. This reduction is carried out in a solvent in the presence of a catalyst in hydrogen atmosphere at 1 to 150 atm by a conventional method. The solvent is exemplified by alcohols such as methanol, ethanol, propanol, isopropanol and 2-methoxyethanol, aromatic hydrocarbons such as benzene, toluene and xylene, ethers such as ethyl ether, isopropyl ether, dioxane and tetrahydrofuran, halogenated hydrocarbons such as chloroform, dichloromethane and 1,1,2,2-tetrachloroethane, ethyl acetate, acetic acid and mixtures thereof. When a metal compound such as a nickel compound, a transition metal such as palladium, platinum or rhodium is used as a catalyst, the reaction is advantageously carried out. Reaction temperature is normally 0° to 100° C., preferably 10° to 80° C., reaction time being 0.5 to 50 hours.

Method C

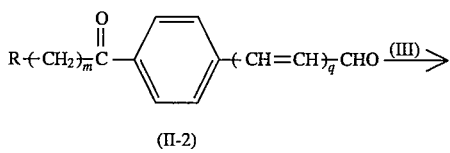

(II-2)

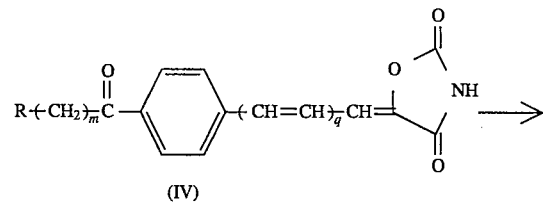

(IV)

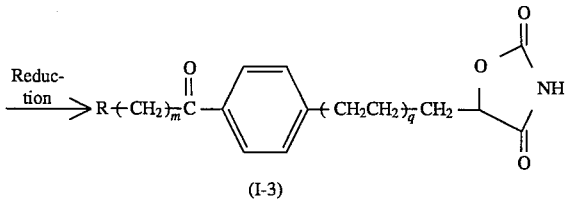

(I-3)

wherein q represents 1 or 2; the other symbols have the same definitions as above.

In this method, aldehyde derivative (II-2) and compound (III) are first reacted to produce compound (IV), which is then subjected to a reduction reaction to produce 2,4-oxazolidinedione derivative (I-3). Reaction of compounds (II-2) with (III) is carried out in the same manner as method A. Reduction of compound (IV) is carried out in the same manner as method B.

The intermediate (IV) in this method may be in (E)-form or (Z)-form at the double bond attached to the 5-position of the oxazolidinedione ring. Though each isomer may be isolated, a mixture of those isomers may be used for the production of compound (I-3) without isolation.

Method D

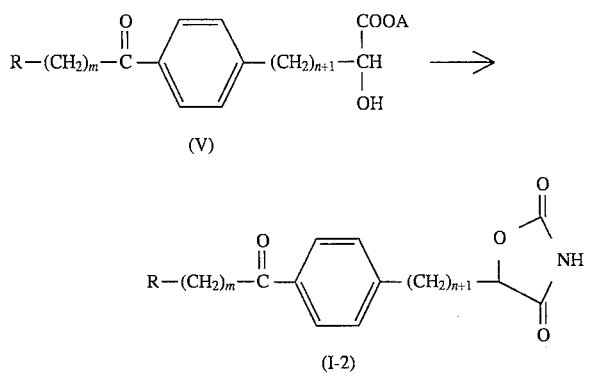

wherein A represents a hydrogen atom or a lower alkyl group; the other symbols have the same definitions as above.

The lower alkyl group for A is exemplified by alkyl groups having 1 to 4 carbon atoms such as methyl, ethyl, propyl, isopropyl, butyl, isobutyl and sec-butyl.

In this method, hydroxycarboxylic acid ester derivative (V) is reacted with an alkali metal cyanate such as potassium cyanate or sodium cyanate in a solvent to yield compound (I-2) as an alkali metal salt, which is then treated with an acid to produce compound (I-2). Reaction of hydroxycarboxylic acid ester derivative (V) and alkali metal cyanate is carried out in an appropriate solvent. The solvent is exemplified by alcohols such as methanol, ethanol, propanol, isopropanol, 2-methoxyethanol and butanol, N,N-dimethylformamide (DMF), dimethyl sulfoxide, acetonitrile and mixtures thereof. The amount of alkali metal cyanate used is normally 1 to 10 mol equivalents, preferably 1 to 5 mol equivalents relative to compound (V). Reaction temperature is normally 0° to 150° C., preferably 10° to 120° C., reaction time being 0.5 to 50 hours. The alkali metal salt of compound (I-2) thus obtained is treated with an acid by a conventional method to produce compound (I-2). This acid treatment is carried out in the presence or absence of an appropriate solvent. The solvent is exemplified by alcohols such as methanol, ethanol, propanol, isopropanol, 2-methoxyethanol and butanol, aromatic hydrocarbons such as benzene, toluene and xylene, ethers such as ethyl ether, isopropyl ether, dioxane and tetrahydrofuran, halogenated hydrocarbons such as chloroform, dichloromethane and 1,1,2,2-tetrachloroethane, ethyl acetate, acetonitrile and mixtures thereof. Although it is preferable to use an inorganic acid such as hydrochloric acid, sulfuric acid, nitric acid or hydrobromic acid in excess, organic acids such as acetic acid, citric acid and tartaric acid can also be used.

Method E

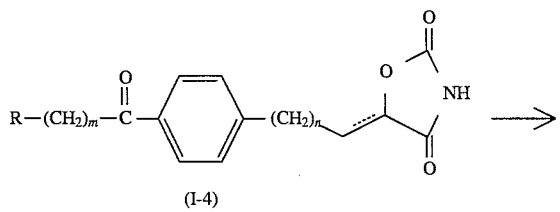

Method E -continued

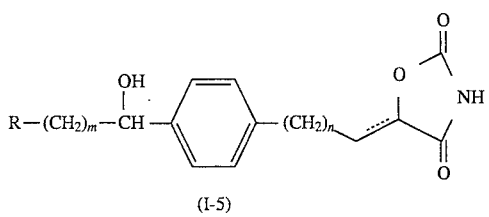

wherein the symbols have the same definitions as above.

In this method, compound (I-4) is subjected to a reduction reaction to produce alcohol derivative (I-5). This reduction can be carried out by a known method. For example, reduction with a metal hydride, reduction with a metal-hydrogen complex compound, and reduction with diborane or substituted borane are used. In other words, this reaction is achieved by treating compound (I-4) with a reducing agent. Reducing agents include metal-hydrogen complex compounds such as alkali metal borohydrides (e.g., sodium borohydride, lithium borohydride) and lithium aluminum hydride, and diborane, which are chosen as appropriate depending on type of compound (I-4). This reaction is carried out in an organic solvent which does not interfere with the reaction. The solvent is exemplified by aromatic hydrocarbons such as benzene, toluene and xylene, halogenated hydrocarbons such as chloroform, carbon tetrachloride, dichloromethane, 1,2-dichloroethane and 1,1,2,2-tetrachloroethane, ethers such as diethyl ether, tetrahydrofuran and dioxane, alcohols such as methanol, ethanol, propanol, isopropanol and 2-methoxyethanol, amides such as N,N-dimethylformamide, and mixtures thereof, chosen as appropriate depending on type of reducing agent. Reaction temperature is normally -20° to 150° C., preferably 0° to 100° C., reaction time being about 1 to 24 hours.

Method F (I-5) 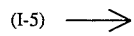

wherein the symbols have the same definitions as above.

In this method, compound (I-5) is subjected to a dehydration reaction to produce compound (I-6). This dehydration can be advantageously carried out by a known method in which compound (I-5) is treated with an acid in a solvent. The acid is exemplified by hydrochloric acid, sulfuric acid, p-toluenesulfonic acid, etc. The solvent is exemplified by aromatic hydrocarbons such as benzene, toluene and xylene, halogenated hydrocarbons such as chloroform, carbon tetrachloride, dichloromethane, 1,2-dichloroethane and 1,1,2,2-tetrachloroethane, ethers such as diethyl ether, tetrahydrofuran and dioxane, alcohols such as methanol, ethanol, propanol, isopropanol and 2-methoxyethanol, amides such as N,N-dimethylformamide, water and mixtures thereof, chosen as appropriate depending on type of acid. Reaction temperature is normally −20° to 150° C., preferably 0° to 100° C., reaction time being about 1 to 24 hours. The compound (I-6) produced in this method may be in (E)-form or (Z)-form relative to a double bond newly formed.

Method G

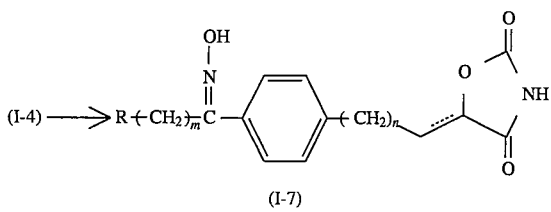

wherein the symbols have the same definitions as above.

In this method, compound (I-4) and hydroxylamine are reacted to produce oximino derivative (I-7). This reaction is carried out by reacting compound (I-4) with an acid salt (e.g., hydrochloride, sulfate, oxalate) of hydroxylamine in a solvent in the presence of a base (e.g., sodium hydroxide, potassium hydroxide, potassium carbonate, sodium carbonate, sodium hydrogen carbonate). The solvent is exemplified by alcohols such as methanol, ethanol, propanol, isopropanol and 2-methoxyethanol, ethers such as diethyl ether, tetrahydrofuran and dioxane, water and mixtures thereof. The amount of hydroxylamine used is preferably 1 to 2 mol equivalents relative to compound (I-4), reaction temperature being normally −20° to 150° C., preferably 0° to 100° C., reaction time being about 30 minutes to 24 hours. The compound (I-7) produced in this method may be in (E)-form or (Z)-form relative to stereochemistry of the hydroxyimino group newly formed.

Method H

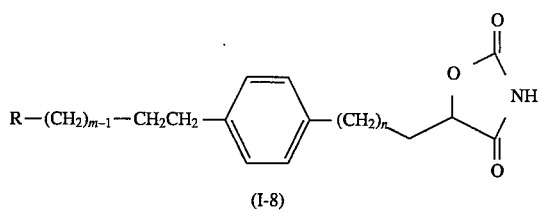

wherein the symbols have the same definitions as above.

In this method, compound (I-6) as produced by method F is subjected to a reduction reaction to produce compound (I-8). This reduction is carried out in the same manner as method B.

Method I

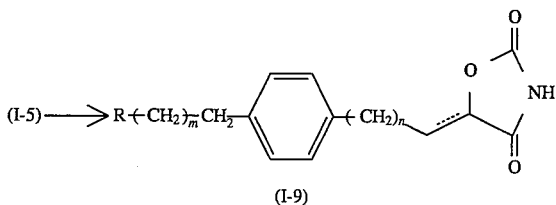

wherein the symbols have the same definitions as above.

In this method, compound (I-5) as produced by method E is subjected to a reduction reaction with a known hydrosilane compound to produce compound (I-9). This reduction is advantageously carried out by reacting compound (I-5) with triethylsilane [$(C_2H_5)_3SiH$] or diethylsilane [$(C_2H_5)_2SiH_2$] in trifluoroacetic acid.

The 2,4-oxazolidinedione derivatives obtained by methods A through I can be isolated and purified by known means of separation and purification such as concentration, reduced-pressure concentration, solvent extraction, crystallization, recrystallization, re-dissolution and chromatography.

Starting material compound (II-2) for method C can be produced by, for example, method J.

Method J

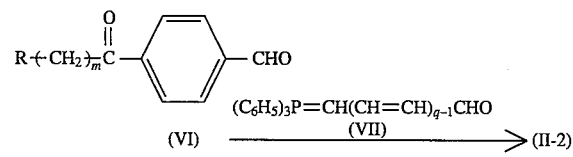

wherein the symbols have the same definitions as above.

In this method, aldehyde derivative (VI) is reacted with (triphenylphosphoranylidene)acetaldehyde or γ-(triphenylphosphoranylidene)crotonaldehyde (VII) to produce unsaturated aldehyde derivative (II-2). Reaction of compounds (VI) and (VII) is carried out in an appropriate solvent by a conventional method. The solvent is exemplified by aromatic hydrocarbons such as benzene, toluene and xylene, ethers such as dioxane, tetrahydrofuran and dimethoxyethane, alcohols such as methanol, ethanol and propanol, N,N-dimethylformamide, dimethyl sulfoxide, chloroform, dichloromethane, 1,2-dichloroethane, 1,1,2,2-tetrachloroethane and mixtures thereof. The amount of compound (VII) used is normally about 1 to 5 mol, preferably about 1 to 3 mol per mol of compound (VI). This reaction is normally carried out at −50° to 150° C., preferably −10° to 100° C., reaction time being about 0.5 to 30 hours. Starting material compound (III) for method A can be produced by, for example, method K or J.

Method K

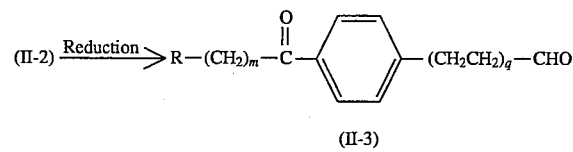

wherein the symbols have the same definitions as above.

In this method, compound (II-2) as produced by method J is subjected to a reduction reaction to produce compound (II-3). This reduction is carried out in the same manner as method B.

Method L

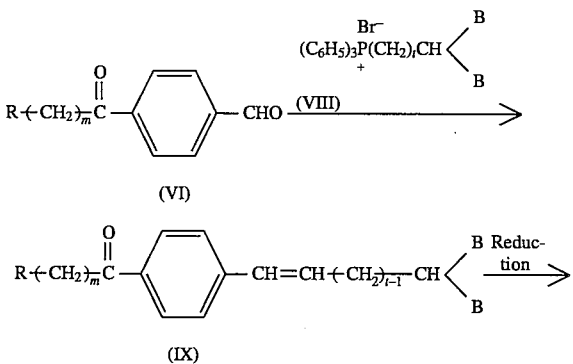

Method L

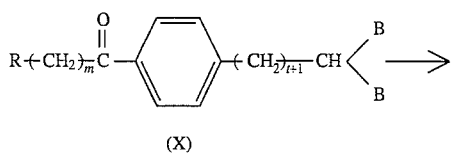

(X)

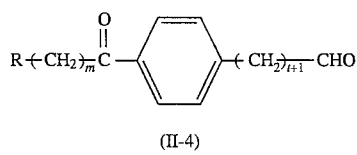

(II-4)

wherein t represents an integer from 1 to 4; B represents a lower alkoxy group, a lower alkylthio group or a lower acyloxy group; the other symbols have the same definitions as above.

The lower alkoxy group for B is exemplified by alkoxy groups having 1 to 4 carbon atoms such as methoxy, ethoxy, propoxy, isopropoxy and butoxy. The lower alkylthio group for B is exemplified by alkylthio groups having 1 to 4 carbon atoms such as methylthio, ethylthio, propylthio, isopropylthio and butylthio. The lower acyloxy group for B is exemplified by acyloxy groups having 1 to 4 carbon atoms such as acetyloxy and propionyloxy. Two B units may bind together to form ethylenedioxy, propylenedioxy, dithiotrimethylene or the like. Accordingly, —CH(B)$_2$ in formulas (VIII), (IX) and (X) is a protected aldehyde group.

In this method, aldehyde derivative (VI) is first reacted with triphenylphosphonium salt (VIII) to produce compound (IX). Compound (IX) is then reduced to compound (X), followed by acid treatment, to produce aldehyde derivative (II-4). Reaction of compounds (VI) and (VIII) is carried out in an appropriate solvent in the presence of a base by a conventional method. The solvent is exemplified by aromatic hydrocarbons such as benzene, toluene and xylene, ethers such as dioxane, tetrahydrofuran and dimethoxyethane, alcohols such as methanol, ethanol and propanol, N,N-dimethylformamide, dimethyl sulfoxide, chloroform, dichloromethane, 1,2-dichloroethane, 1,1,2,2-tetrachloroethane and mixtures thereof. The base is exemplified by alkali metal salts such as sodium hydroxide, potassium hydroxide and potassium carbonate, amines such as pyridine, triethylamine and N,N-dimethylaniline, metal hydrides such as sodium hydride and potassium hydride, sodium ethoxide, sodium methoxide and potassium tert-butoxide. The amount of these bases used is preferably about 1 to 5 mol per mol of compound (VIII). The amount of compound (VIII) used is about 1 to 5 mol, preferably 1 to 3 mol per mol of compound (VI). This reaction is normally carried out at −50° to 150° C., preferably −10° to 100° C., reaction time being 0.5 to 30 hours. Reduction of compound (IX) to compound (X) is carried out in the same manner as method B. Conversion of compound (X) into compound (II-4) can be advantageously carried out by a known method in which compound (X) is treated with an acid in a hydrated solvent. Although it is preferable to use an inorganic acid such as hydrochloric acid, sulfuric acid, nitric acid or hydrobromic acid in excess, organic acids such as acetic acid, citric acid, tartaric acid and p-toluenesulfonic acid can also be used. The solvent is exemplified by ethers such as diethyl ether, tetrahydrofuran and dioxane, alcohols such as methanol, ethanol, propanol, isopropanol and 2-methoxyethanol, amides such as N,N-dimethylformamide, acetonitrile, acetone and mixtures thereof, chosen as appropriate. Reaction temperature is normally −20° to 150° C., preferably 0° to 100° C., reaction time being about 10 minutes to 24 hours.

The aldehyde derivatives obtained by methods J through L can be isolated and purified by known means of separation and purification such as concentration, reduced-pressure concentration, solvent extraction, crystallization, recrystallization, re-dissolution and chromatography.

Starting material compound (V) for method D can be produced by, for example, method M.

Method M

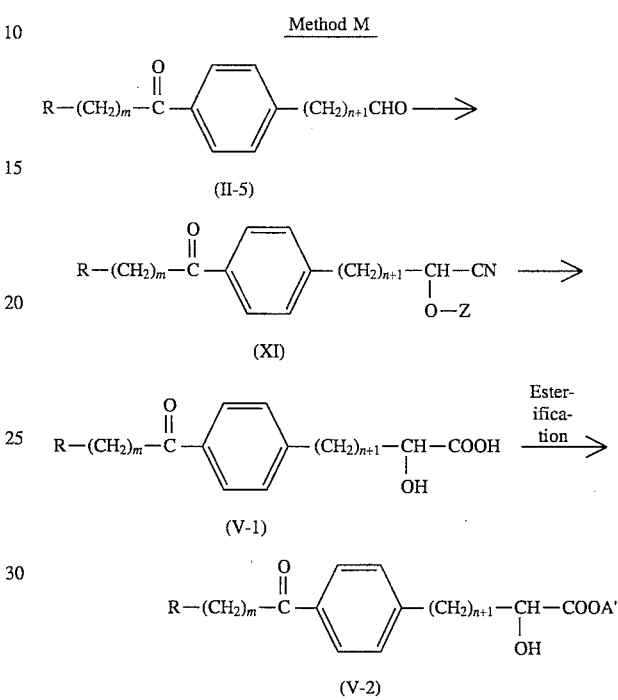

wherein Z represents an acetyl group or a hydrogen atom; A' represents a lower alkyl group; the other symbols have the same definitions as above.

The lower alkyl group for A' is exemplified by the same lower alkyl groups mentioned for A above.

In this method, compounds (V-1) and (V-2) are produced from the aldehyde derivatives produced by methods J through K. Cyano group addition reaction for aldehyde derivative (II-5) is carried out by a known method. For example, compound (II-5) is reacted with potassium cyanide or sodium cyanide in a hydrated solvent in the presence of an acid to produce compound (XI) wherein Z is hydrogen, or reacted with potassium cyanide or sodium cyanide in the presence of acetic anhydride to produce compound (XI) wherein Z is an acetyl group. Compound (V-1) is subjected to acid hydrolysis to produce hydroxy acid (V-1); compound (V-1) is esterified to produce compound (V-2).

Benzaldehyde derivative (VI), a starting material compound for methods J and L can be synthesized by, for example, the methods described in the Journal of Medicinal Chemistry, Vol. 35, p. 1858 (1992), Japanese Patent Unexamined Publication Nos. 272573/1989(corresponding to U.S. Pat. No. 5,061,717) and 272574/1989 (corresponding to WO89/08651 which is based on PCT/US88/00733, filed 8 March 1988) and other publications.

Aldehyde derivative (II-6) including the starting compound (II-2) in Method C can also be produced by method N.

Method N

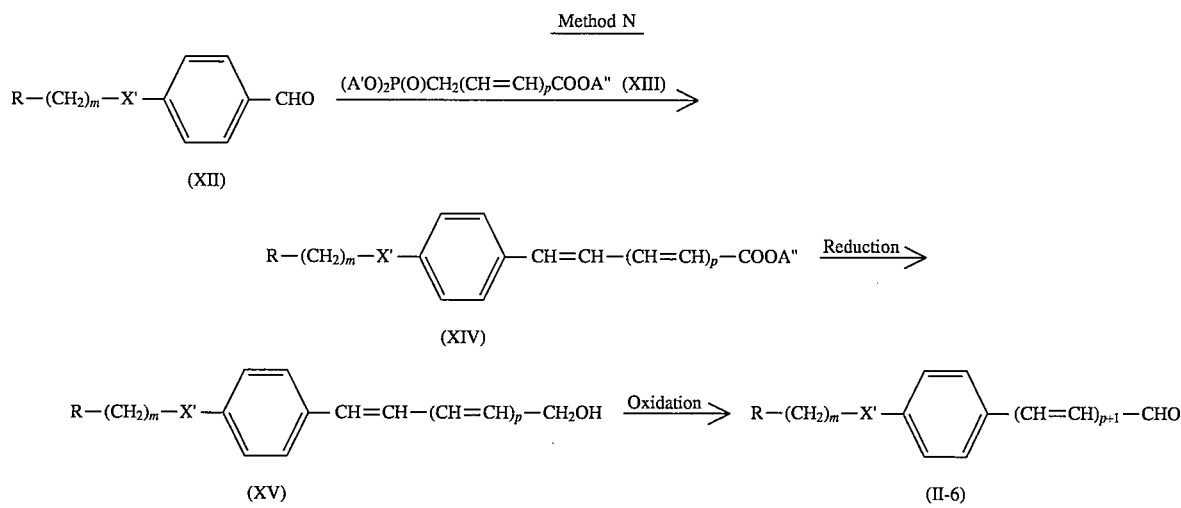

[In formulas (XII), (XIV), (XV) and (II-6), X' represents —$CH_2$— or —$C(=O)$—; in formulas (XIII) and (XIV), A" represents a lower alkyl group; in formulas (XIII), (XIV), (XV) and (II-6), p represents 0 or 1; the other symbols have the same definitions as above.]

The lower alkyl group for A" is exemplified by the same lower alkyl groups specified for A' above.

In this method, aldehyde derivative (XII) is first reacted with a phosphonoacetic acid derivative or γ-phosphonocrotonic acid derivative (XIII) to yield unsaturated ester derivative (XIV). The reaction of compounds (XII) with (XIII) is carried out in the same manner as the reaction of compounds (VI) with (VIII) in method L.

Compound (XIV) is then reduced to alcohol derivative (XV). This reducing reaction can be carried out by a known method. For example, reduction with a metal hydride, reduction with a metal-hydrogen complex compound, and reduction with diborane or substituted borane are used. In other words, this reaction is achieved by treating compound (XIV) with a reducing agent. Reducing agents include metal-hydrogen complex compounds such as alkali metal borohydrides (e.g., sodium borohydride, lithium borohydride) and lithium aluminum hydride, and diborane. It is advantageous to use diisobutyl aluminum hydride. This reaction is carried out in an organic solvent which does not interfere with the reaction. The solvent is exemplified by aromatic hydrocarbons such as benzene, toluene and xylene, halogenated hydrocarbons such as chloroform, carbon tetrachloride, dichloromethane, 1,2-dichloroethane and 1,1,2,2-tetrachloroethane, ethers such as diethyl ether, tetrahydrofuran and dioxane, alcohols such as methanol, ethanol, propanol, isopropanol and 2-methoxyethanol, amides such as N,N-dimethylformamide, and mixtures thereof, chosen as appropriate depending on type of reducing agent. Reaction temperature is normally –20° to 150° C., preferably 0° to 100° C., reaction time being about 1 to 24 hours.

Compound (XV) is then oxidized to aldehyde (II-6). This oxidizing reaction can be carried out by a known method. For example, oxidation with manganese dioxide, oxidation with chromic acid, and oxidation with dimethyl sulfoxide are used. In other words, this reaction is achieved by treating compound (XV) with an oxidizing agent. Oxidizing agents include manganese dioxide and chromic anhydride. It is advantageous to use manganese dioxide. This reaction is carried out in an organic solvent which does not interfere with the reaction. The solvent is exemplified by aromatic hydrocarbons such as benzene, toluene and xylene, halogenated hydrocarbons such as chloroform, carbon tetrachloride, dichloromethane, 1,2-dichloroethane and 1,1,2,2-tetrachloroethane, ethers such as diethyl ether, tetrahydrofuran and dioxane, dimethyl sulfoxide, and mixtures thereof, chosen as appropriate depending on type of oxidizing agent. Reaction temperature is normally –20° to 150° C., preferably 0° to 100° C., reaction time being about 1 to 24 hours.

Aldehyde derivative (II-6) thus obtained can be isolated and purified by known means of separation and purification such as concentration, reduced-pressure concentration, solvent extraction, crystallization, recrystallization, re-dissolution and chromatography.

Starting material compound (XII) for method N wherein X' is —$CH_2$— and m is 1 can be produced by, for example, method O or P.

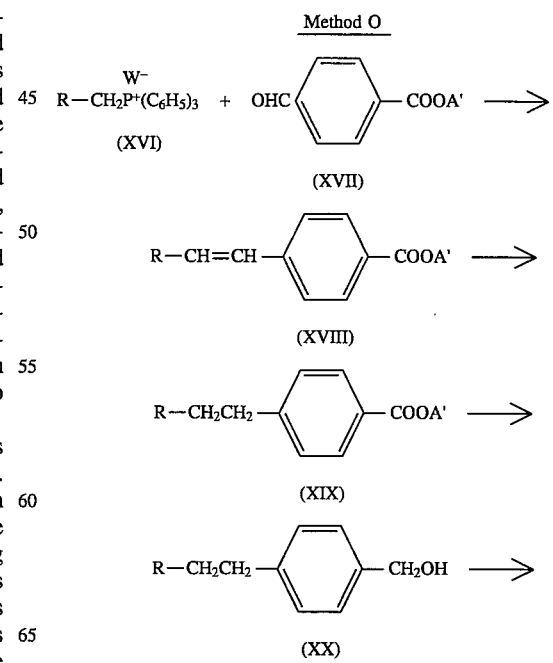

Method O

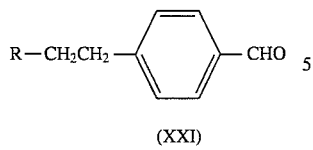

(XXI)

[With respect to formula (XVI), W represents a halogen atom; the other symbols have the same definitions as above.]

The halogen atom for W is exemplified by chlorine, bromine and iodine.

In this method, phosphonium salt (XVI) and aldehyde derivative (XVII) are condensed together to yield compound (XVIII). This condensing reaction is carried out in the same manner as the reaction of compounds (VI) and (VIII) in method L. Compound (XVIII) is obtained as a mixture of (E)-and (Z)-configuration isomers with respect to the newly formed double bond. With respect to the (E)- and (Z)-configurations, each after isolation, or their mixture without isolation, is subjected to a reducing reaction in the same manner as in method B to yield compound (XIX). Compound (XIX) is then treated in the same manner as the reduction of compound (XIV) to compound (XV) in method N, to yield alcohol derivative (XX). Alcohol derivative (XX) is treated in the same manner as the oxidation of compound (XV) to compound (II-6) in method N, to yield aldehyde derivative (XXI).

Aldehyde derivative (XXI) thus obtained can be isolated and purified by known means of separation and purification such as concentration, reduced-pressure concentration, solvent extraction, crystallization, recrystallization, re-dissolution and chromatography.

Method P

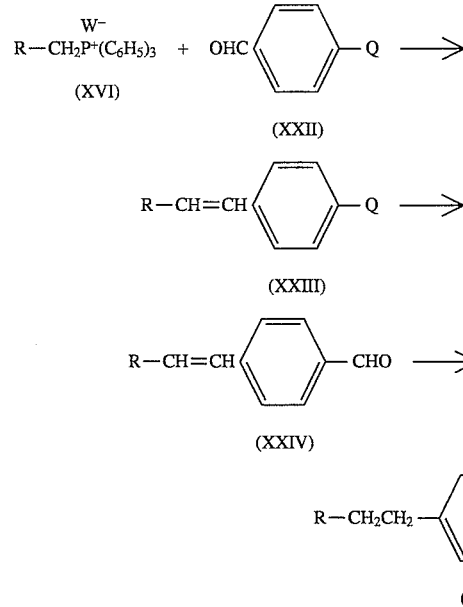

[With respect to formulas (XXII) and (XXIII), Q represents a halogen atom; the other symbols have the same definitions as above.]

The halogen atom for Q is exemplified by chlorine, bromine and iodine.

In this method, phosphonium salt (XVI) and aldehyde derivative (XXII) are condensed together to yield compound (XXIII). This condensing reaction is carried out in the same manner as the reaction of compounds (VI) and (VIII) in method L. Compound (XXIII) is obtained as a mixture of (E)- and (Z)-configuration isomers with respect to the newly formed double bond. With respect to the (E)- and (Z)-configurations, each after isolation, or their mixture without isolation, is treated with butyllithium, sec-butyllithium, tert-butyllithium, methyllithium, phenyllithium or the like to yield a lithio compound, which is then reacted with N,N-dimethylformamide (DMF) to yield compound (XXIV). The reaction of compound (XXIII) to compound (XXIV) is preferably carried out at −100° to 50° C. over a period of about 1 to 24 hours, with an ether such as diethyl ether, tetrahydrofuran or dioxane as a solvent. The amount of N,N-dimethylformamide (DMF) used is 1 to 5 mol equivalents relative to compound (XXIII). Compound (XXIV) is subjected to a reducing reaction in the same manner as method B to yield compound (XXI).

Aldehyde derivatives (XXI) and (XXIV) thus obtained can be isolated and purified by known means of separation and purification such as concentration, reduced-pressure concentration, solvent extraction, crystallization, recrystallization, re-dissolution and chromatography.

Intermediate (XXIV) for method P can also be produced by method Q.

Method Q

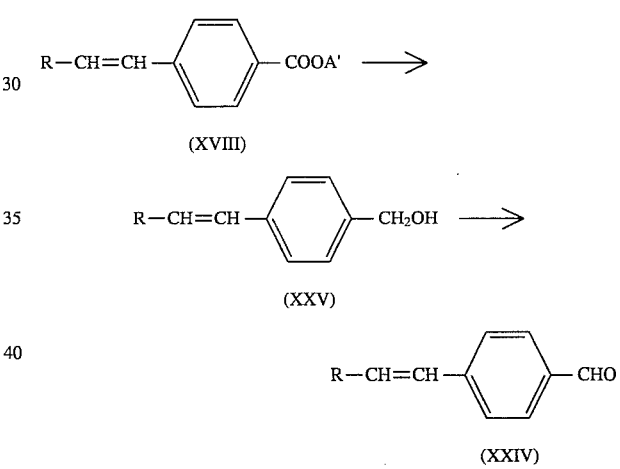

[The symbols have the same definitions as above.]

In this method, compound (XVIII) is first treated in the same manner as the reducing reaction of compound (XIV) in method N, to yield compound (XXV), which is then treated in the same manner as the oxidation reaction of compound (XV) in method N, to yield compound (XXIV).

Aldehyde derivative (XXIV) thus obtained can be isolated and purified by known means of separation and purification such as concentration, reduced-pressure concentration, solvent extraction, crystallization, recrystallization, re-dissolution and chromatography.

Compound (I) can also be produced by the following methods R through W.

Method R

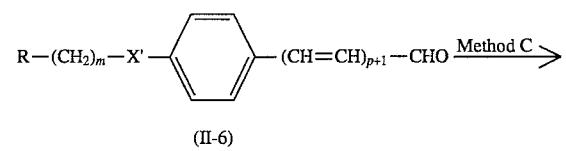

-continued
Method R

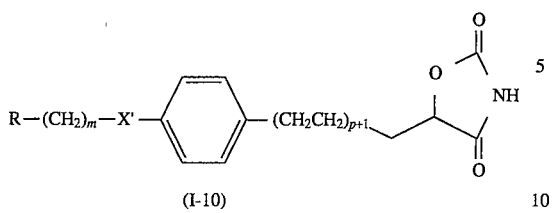

(I-10)

[The symbols have the same definitions as above.]

In this method, aldehyde derivative (II-6) as produced by method N is treated by method C to yield compound (I-10).

2,4-oxazolidinedione derivative (I-10) thus obtained can be isolated and purified by known means of separation and purification such as concentration, reduced-pressure concentration, solvent extraction, crystallization, recrystallization, re-dissolution and chromatography.

Method S

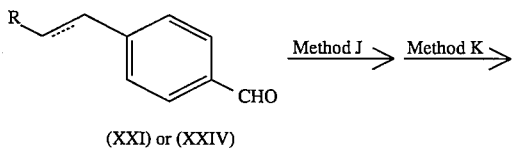

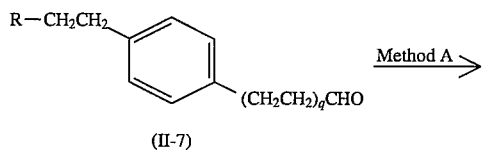

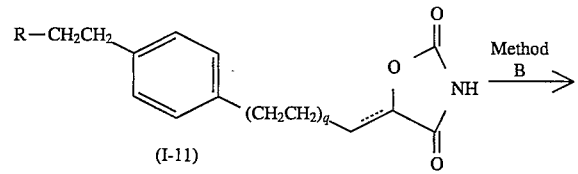

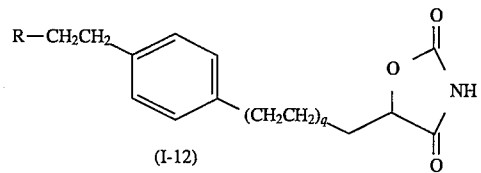

[The symbols have the same definitions as above.]

In this method, aldehyde derivative (XXI) as produced by method O or P or aldehyde derivative (XXIV) as produced by method P or Q is treated by method J and then method K to yield aldehyde derivative (II-7), which is then treated by method A to yield compound (I-11), which is then treated by method B to yield compound (I-12).

2,4-oxazolidinedione derivatives (I-11) and (I-12) thus obtained can be isolated and purified by known means of separation and purification such as concentration, reduced-pressure concentration, solvent extraction, crystallization, recrystallization, re-dissolution and chromatography.

Method T

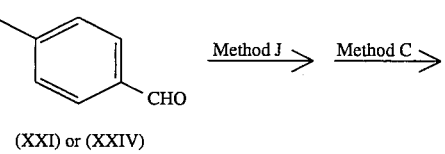

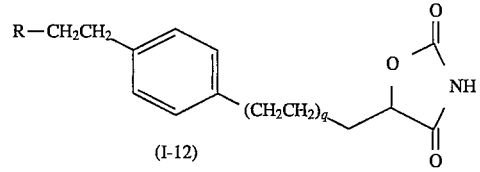

[The symbols have the same definitions as above.]

In this method, aldehyde derivative (XXI) as produced by method O or P or aldehyde derivative (XXIV) as produced by method P or Q is treated by method J and then method C to yield compound (I-12).

2,4-oxazolidinedione derivative (I-12) thus obtained can be isolated and purified by known means of separation and purification such as concentration, reduced-pressure concentration, solvent extraction, crystallization, recrystallization, re-dissolution and chromatography.

Method U

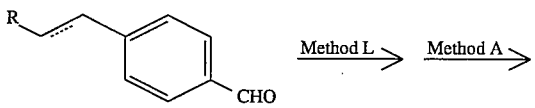

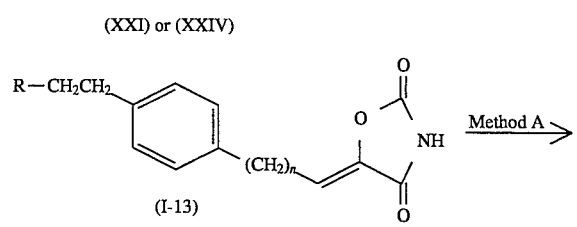

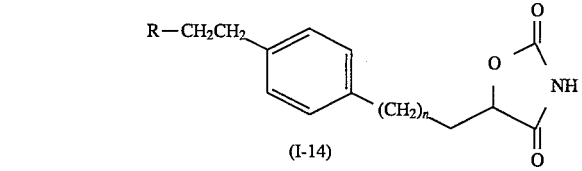

[The symbols have the same definitions as above.]

In this method, aldehyde derivative (XXI) as produced by method O or P or aldehyde derivative (XXIV) as produced by method P or Q is treated by method L and then method A to yield compound (I-13), which is then treated by method B to yield compound (I-14).

2,4-oxazolidinedione derivatives (I-13) and (I-14) thus obtained can be isolated and purified by known means of separation and purification such as concentration, reduced-pressure concentration, solvent extraction, crystallization, recrystallization, re-dissolution and chromatography.

Method V

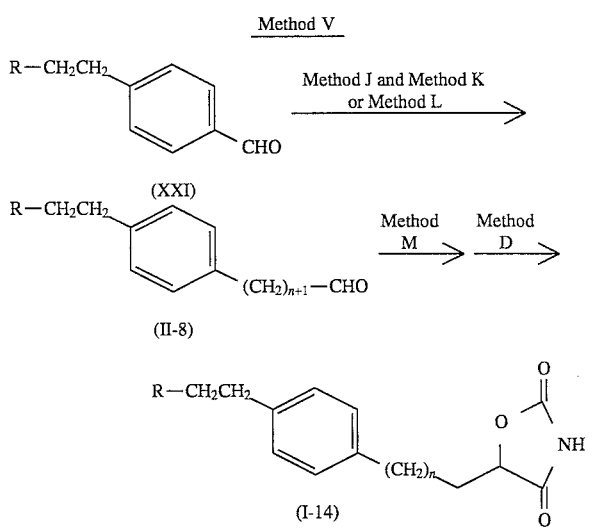

[The symbols have the same definitions as above.]

In this method, aldehyde derivative (XXI) as produced by method O or P is treated by method J and then method K or by method L alone, to yield aldehyde derivative (II-8), which is then treated by method M and then method D to yield compound (I-14).

2,4-oxazolidinedione derivative (I-14) thus obtained can be isolated and purified by known means of separation and purification such as concentration, reduced-pressure concentration, solvent extraction, crystallization, recrystallization, re-dissolution and chromatography.

Starting material compound (XVI) for methods O and P can be produced by method W.

Method W

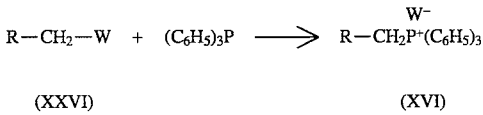

[The symbols have the same definitions as above.]

In this method, a compound represented by general formula (XXVI) is reacted with a reactive amount of triphenylphosphine to yield a phosphonium salt derivative represented by general formula (XVI). This reaction is carried out in a solvent. The solvent is exemplified by aromatic hydrocarbons such as benzene, toluene and xylene, ethers such as tetrahydrofuran, dioxane and dimethoxyethane, acetonitrile and mixtures thereof. This reaction is normally carried out at 10° to 200° C., preferably 30° to 150° C. over a period of 0.5 to 50 hours.

Effect of the Invention

Compound (I) relating to the present invention possesses hypoglycemic and hypolipidemic activity. Experimental data supporting this fact are given below.

Experimental Example

Hypoglycemic and hypolipidemic action in mice

KKA$^y$ mice at 9–14 weeks of age were fed on powdered diet (CE-2, Clea Japan) containing the subject compound at 0.005% for 4 days. Animals had free access to water during experimental period. Blood was collected via the orbital cavity venous plexus; plasma glucose and triglyceride were determined by the enzyme method using the Iatrochem-GLU (A) and Iatro-MA701 TG kits (IATRON LABORATORIES, INC.), respectively. Figures for percent reduction rates relative to the control group are given in Table 1.

TABLE 1

| Compound (Example number) | Hypoglycemic action (%) | Hypolipidemic action (%) |
|---|---|---|
| 1 | 32 | 17 |
| 3 | 51 | 38 |
| 4 | 22 | 19 |
| 8 | 46 | 37 |
| 9 | 49 | 49 |
| 10 | 61 | 71 |
| 11 | 46 | 47 |
| 13 | 40 | 65 |

As is evident from these results, oxazolidinedione derivative (I) relating to the present invention possesses excellent hypoglycemic and hypolipidemic activities in non-insulin-dependent diabetes mellitus model mouse, and is pharmaceutically useful as a therapeutic agent for diabetes mellitus, hyperlipidemia and hypertension, for example.

EXAMPLES

Example 1

A mixture of 5-[4-[3-(5-methyl-2-phenyl-4-oxazolyl)propionyl]cinnamylidene]-2,4-oxazolidinedione (1.02 g), palladium-carbon (5%, 0.5 g) and tetrahydrofuran (THF) (150 ml) was subjected to catalytic hydrogenation at 1 atm and room temperature. After the catalyst was filtered out, the filtrate was concentrated under reduced pressure. The residue was purified by silica gel column chromatography. From the fraction eluted with chloroform-methanol (100:3), 5-[3-[4-[3-(5-methyl-2-phenyl-4-oxazolyl)propionyl]phenyl]propyl]-2,4-oxazolidinedione (0.58 g, 56%) was obtained, which was then recrystallized from dichloromethane-methanol to yield colorless needles having a melting point of 184°–185° C.

Example 2

To a solution of 5-[3-[4-[3-(5-methyl-2-phenyl-4-oxazolyl)propionyl]phenyl]propyl]-2,4-oxazolidinedione (0.25 g) in tetrahydrofuran (THF) (10 ml)-ethanol (10 ml), sodium borohydride (0.05 g) was added, followed by stirring at room temperature for 2 hours. The reaction mixture was poured over water, neutralized with 2N HCl and then extracted with ethyl acetate. The ethyl acetate layer was washed with water, dried (MgSO$_4$) and then concentrated under reduced pressure; the residue was purified by silica gel column chromatography. From the fraction eluted with ethyl acetate-chloroform (1:1), 5-[3-[4 -[1-hydroxy-3-(5-methyl-2-phenyl-4oxazoly) propyl]phenyl]propyl]-2,4-oxazolidinedione (0.16 g, 64%) was obtained, which was then recrystallized from acetone-isopropyl ether to yield colorless needles having a melting point of 150°–151° C.

Example 3

A mixture of 5-[3-[4-[1-hydroxy-3-(5-methyl-2-phenyl-4-oxazolyl)propyl]phenyl]propyl]-2,4-oxazolidinedione (0.17 g), 9N HCl (10 ml) and tetrahydrofuran (THF) (10 ml) was heated under refluxing conditions for 2 hours. The reaction mixture was concentrated under reduced pressure; the residue was poured over water and extracted with ethyl acetate. The ethyl acetate layer was washed with water, dried (MgSO$_4$) and then concentrated under reduced pressure; the residue was purified by silica gel column chromatography. From the fraction eluted with chloroform-methanol (100:2), 5-[3-[4-[3-(5-methyl-2-phenyl-4-oxazolyl)-1-propenyl]phenyl]propyl]-2,4oxazolidinedione (0.045 g, 28%) was obtained, which was then recrystallized from ether-isopropyl ether to yield colorless needles having a melting point of 136°–137° C.

Example 4

A mixture of 5-[3-[4-[1-hydroxy-3-(5-methyl-2-phenyl-4-oxazolyl)propyl]phenyl]propyl]-2,4-oxazolidinedione (0.14 g), triethylsilane [(C$_2$H$_5$)$_3$SiH] (0.075 g) and trifluoroacetic acid (2 ml) was stirred at room temperature for 3 hours. The reaction mixture was poured over water, neutralized with an aqueous solution of sodium hydrogen carbonate and then extracted with ethyl acetate. The ethyl acetate layer was washed with water, dried (MgSO$_4$) and then concentrated under reduced pressure; the residue was purified by silica gel column chromatography. From the fraction eluted with chloroform-methanol (100:3), 5-[3-[4-[3-(5-methyl-2-phenyl-4-oxazolyl)propyl]phenyl]propyl]-2,4-oxazolidinedione (0.11 g, 82%) was obtained, which was then recrystallized from ether-methanol to yield colorless needles having a melting point of 119°–120° C.

Example 5

A mixture of 5-[3-[4-[3-(5-methyl-2-phenyl-4-oxazolyl)propionyl]phenyl]propyl]-2,4-oxazolidinedione (0.28 g), hydroxylamine hydrochloride (0.09 g), sodium acetate (0.11 g) and 80% methanol (20 ml) was stirred under refluxing conditions for 2 hours. The reaction mixture was poured over water; the resulting crystal was collected by filtration to yield 5-[3-[4-[1-hydroxyimino-3-(5-methyl-2-phenyl-4-oxazolyl)propyl]phenyl]propyl]-2,4-oxazolidinedione (0.26 g, 90%), which was then recrystallized from dichloromethane-methanol to yield colorless prisms having a melting point of 185°–186° C.

Example 6

A mixture of 2-hydroxy-4-[4-[3-(5-methyl-2-phenyl-4-oxazolyl)propionyl]phenyl]butyric acid ethyl ester (1.43 g), powdered potassium cyanate (0.83 g) and butanol (30 ml) was heated under refluxing conditions for 2 days. After the solvent was distilled off under reduced pressure, the residue was acidified with 2N hydrochloric acid and then extracted with ethyl acetate. The ethyl acetate layer was washed with water, dried (MgSO$_4$) and then concentrated. The residue was purified by silica gel column chromatography. From the fraction eluted with chloroform-methanol (100:2), 5-[2-[4-[3-(5-methyl-2-phenyl-4-oxazolyl)propionyl]phenyl]ethyl]-2,4-oxazolidinedione (0.56 g, 39%) was obtained, which was then recrystallized from dichloromethane-methanol to yield colorless prisms having a melting point of 173°–174° C.

Example 7

5-[2-[4-[3-(5Methyl-2-phenyl-4-oxazolyl)propionyl]phenyl]ethyl]-2,4-oxazolidinedione was treated in the same manner as in Example 2 to yield 5[-2-[4-[1-hydroxy-3-(5-methyl-2-phenyl-4-oxazoly)propyl]phenyl]ethyl]-2,4-oxazolidinedione, which was then recrystallized from dichloromethane-methanol to yield colorless needles having a melting point of 145°–146° C.

Example 8

A mixture of 5-[2-[4-[1-hydroxy-3-(5-methyl-2-phenyl-4-oxazolyl)propyl]phenyl]ethyl]-2,4-oxazolidinedione (0.32 g), p-toluenesulfonic acid monohydrate (p-TsOH.H$_2$O) (0.145 g) and toluene (40 ml) was stirred under refluxing conditions for 2 hours. The reaction mixture was washed with an aqueous solution of sodium hydrogen carbonate and water, dried (MgSO$_4$) and then concentrated under reduced pressure. The residue was purified by silica gel column chromatography. From the fraction eluted with chloroform-methanol (100:2), 5-[2-[4-[3-(5-methyl-2-phenyl-4-oxazolyl)-1-propenyl]phenyl]ethyl]-2,4-oxazolidinedione (0.235 g, 77%) was obtained, which was then recrystallized from dichloromethane-isopropyl ether to yield colorless needles having a melting point of 175°–176° C.

Example 9

A mixture of 5-[4-[3-(5-methyl-2-phenyl-4-oxazolyl)propionyl]benzylidene]-2,4-oxazolidinedione (0.75 g), palladium-carbon (5%, 0.75 g) and tetrahydrofuran (THF) (70 ml) was subjected to catalytic hydrogenation at 3 atm and room temperature. After the catalyst was filtered out, the filtrate was concentrated under reduced pressure. The residue was purified by silica gel column chromatography. From the fraction eluted with chloroform-ethyl acetate (1:1, v/v), 5-[4-[1-hydroxy-3-(5-methyl-2-phenyl-4-oxazolyl)propyl]benzyl]-2,4-oxazolidinedione (0.4 g, 53%) was obtained, which was then recrystallized from dichloromethane-methanol-isopropyl ether to yield colorless needles having a melting point of 154°–155° C.

Example 10

A mixture of 5-[4-[1-hydroxy-3-(5-methyl-2-phenyl-4-oxazolyl)propyl]benzyl]-2,4-oxazolidinedione (0.21 g), p-toluenesulfonic acid monohydrate (p-TsOH.H$_2$O) (0.1 g) and toluene (40 ml) was stirred under refluxing conditions for 2 hours. The reaction mixture was washed with an aqueous solution of sodium hydrogen carbonate and water, dried (MgSO$_4$) and then concentrated under reduced pressure. The residue was purified by silica gel column chromatography. From the fraction eluted with chloroform-methanol (100:2), 5-[4-[3-(5-methyl-2-phenyl-4-oxazolyl)-1-propenyl]benzyl]-2,4-oxazolidinedione (0.14 g, 70%) was obtained, which was then recrystallized from dichloromethane-isopropyl ether to yield colorless needles having a melting point of 168°–169° C.

Example 11

A mixture of (E)-4-[2-[5-methyl-2-(2-naphthyl)-4-oxazolyl]vinyl]cinnamaldehyde (2.00 g), 2,4-oxazolidinedione (1.11 g), piperidine (0.23 g), ethanol (100 ml) and tetrahydrofuran (50 ml) was refluxed under heating conditions for 8 hours. After the reaction mixture was concentrated, chloroform was added to the residue; the mixture was then washed with 2N HCl and water. The organic layer was washed with water, dried (MgSO$_4$) and then concentrated. The residue was subjected to silica gel column chromatography. The crystal obtained from the fraction eluted with ethyl acetate-chloroform (1:9, v/v) was dissolved in tetrahydrofuran (100 ml), and subjected to catalytic hydrogenation at 1 atm and room temperature in the presence of palladium-carbon (5%, 0.5 g). After the catalyst was filtered off, the filtrate was concentrated under reduced pressure. The residue was subjected to silica gel column chromatography to yield 5-[3-[4-[2-[5-methyl-2-(2-naphthyl)-4-oxazolyl]ethyl]phenyl]propyl]-2,4-oxazolidinedione (0.29 g, 12%) from the fraction eluted with methanol-chloroform (2:98, v/v), which was then recrystallized from dichloromethane-isopropyl ether to yield a colorless prisms having a melting point of 168°–169° C.

Example 12

To a mixture of 5-[4-[2-(5-methyl-4-phenyl-2-thiazolyl)ethyl]cinnamylidene]-2,4-oxazolidinedione (0.55 g) (mixture of the (E)- and (Z)-configurations) as obtained in Reference Example 28 and dioxane (50 ml), palladium-carbon (5%, 2.0 g) was added, followed by catalytic reduction at 1 atm and room temperature. After the catalyst was filtered off, the filtrate was concentrated under reduced pressure to yield 5-[3-[4-[2-(5-methyl-4-phenyl-2-thiazolyl)ethyl]phenyl]propyl]-2,4-oxazolidinedione (0.48 g, 86%), which was then recrystallized from ethyl acetate-hexane to yield colorless prisms having a melting point of 111°–112° C.

Example 13

(E,E)-5-[4-[2-(5-Methyl-2-phenyl-4-oxazolyl)vinyl]cinnamylidene]-2,4-oxazolidinedione was subjected to catalytic reduction in the same manner as in Example 12 to yield 5-[3-[4-[2-(5-methyl-2-phenyl-4-oxazolyl)ethyl]phenyl]propyl]-2,4-oxazolidinedione, which was then recrystallized from ethyl acetate-hexane to yield colorless prisms having a melting point of 112°–113° C.

Example 14

A mixture of 5-[(E,E)-5-[4-[2-(5-methyl2-phenyl-4-oxazolyl)ethyl]phenyl]-2,4-pentadienylidene]-2,4-oxazolidinedione (0.84 g) [mixture of the (E)- and (Z)-configurations] as obtained in Reference Example 51, palladium-carbon (5%, 0.3 g) and dioxane (50 ml) was subjected to catalytic hydrogenation at 1 atm and room temperature. After the catalyst was filtered off, the filtrate was concentrated under reduced pressure. The residue was subjected to silica gel chromatography to yield 5-[5-[4-[2-(5-methyl-2-phenyl-4-oxazolyl) ethyl]phenyl]pentyl]-2,4-oxazolidinedione (0.79 g, 93%) from the fraction eluted with chloroform-ethyl acetate (10:1, v/v), which was then recrystallized from ethyl acetate-hexane to yield colorless prisms having a melting point of 116°–117° C.

Example 15

To a mixture of 5-[4-[(E)-2-[2-(2-furyl)-5-methyl-4-oxazolyl]vinyl]cinnamylidene]-2,4-oxazolidinedione (0.25 g) [mixture of the (E)- and (Z)-configurations] as obtained in Reference Example 52 and ethyl acetate (15 ml), palladium-carbon (5%, 0.1 g) was added, and catalytic hydrogenation was conducted at 1 atm and room temperature. After the catalyst was filtered off, the filtrate was concentrated under reduced pressure. The residue was subjected to silica gel chromatography to yield 5-[3-[4-[2-[2-(2-furyl)-5-methyl-4-oxazolyethyl]phenyl]propyl]-2,4-oxazolidinedione (0.225 g, 89%) from the fraction eluted with chloroform-ethyl acetate (10:1, v/v), which was then recrystallized from ethyl acetate-hexane to yield colorless needles having a melting point of 123°–124° C.

Example 16

A mixture of ethyl 2-hydroxy-6-[4-[2-[2-(2-furyl)-5-methyl-4-oxazolyl]ethyl]phenyl]hexanoate (0.55 g) as obtained in Reference Example 50, potassium cyanate (0.542 g) and butanol (30 ml) was heated under refluxing conditions for 50 hours. The reaction mixture was concentrated under reduced pressure; 0.5 N HCl (50 ml) was added to the residue, followed by extraction with ethyl acetate. The ethyl acetate layer was washed with water, dried (MgSO$_4$), and then concentrated under reduced pressure. The residue was subjected to silica gel chromatography to yield 5-[4-[4-[2-[2-(2-furyl) -5-methyl-4-oxazolyl]ethyl]phenyl]butyl]-2,4-oxazolidinedione (0.22 g, 40%) from the fraction eluted with chloroform-ethyl acetate (10:1, v/v), which was then recrystallized from ethyl acetate-hexane to yield colorless needles having a melting point of 140°–141 ° C.

Formulation Example 1 (Production of Tablets)

| | |
|---|---|
| (1) 5-[4-[3-(5-methyl-2-phenyl-4-oxazolyl)-1-propenyl]phenyl]ethyl]-2,4-oxazolidinedione(compound produced in Example 8) | 10 g |
| (2) Lactose | 50 g |
| (3) Corn starch | 15 g |
| (4) Carboxymethyl cellulose calcium | 44 g |
| (5) Magnesium stearate | 1 g |
| 1000 tablets | 120 g |

The entire amounts of components (1), (2) and (3) and 30 g of component (4) were kneaded with water and vacuum dried, followed by particle size uniformization. To the size-uniformized powder, 14 g of component (4) and 1 g of component (5) were added; the mixture was tableted using a tableting machine, to yield 1000 tablets each containing 10 mg of component (1).

Formulation Example 2 (Production of Tablets)

| | |
|---|---|
| (1) 5-[3-[4-[3-(5-methyl-2-phenyl-4-oxazoly-1-propenyl]phenyl]propyl]-2,4-oxazolidinedione (compound produced in Example 3) | 30 g |
| (2) Lactose | 50 g |
| (3) Corn starch | 15 g |
| (4) Carboxymethyl cellulose calcium | 44 g |
| (5) Magnesium stearate | 1 g |
| 1000 tablets | 140 g |

The entire amounts of components (1), (2) and (3) and 30 g of component (4) were kneaded with water and vacuum dried, followed by particle size uniformization. To the size-uniformized powder, 14 g of component (4) and 1 g of component (5) were added; the mixture was tableted using a tableting machine, to yield 1000 tablets each containing 30 mg of component (1).

Reference Example 1

A mixture of 4-[3-(5-methyl-2-phenyl-4-oxazolyl)propionyl]benzaldehyde (6.0 g), (triphenylphosphoranylidene)acetaldehyde [(C$_6$H$_5$)$_3$P=CHCHO](6.29 g) and benzene (100 ml) was stirred under refluxing conditions for 24 hours. The reaction mixture was concentrated under reduced pressure; the residue was subjected to silica gel column chromatography. From the fraction eluted with ethyl acetate-hexane (1:2), 4-[3-(5-methyl-2-phenyl-4-oxazolyl)propionyl]cinnamaldehyde (4.08 g, 63%) was obtained, which was then recrystallized from dichloromethane-isopropyl ether to yield colorless prisms having a melting point of 119°–120° C.

Reference Example 2

A mixture of 4-[3-(5-methyl-2-phenyl-4-oxazolyl)propionyl]cinnamaldehyde (3.60 g), 2,4-oxazolidinedione (1.58 g), piperidine (0.27 g) and acetic acid (30 ml) was heated under refluxing conditions for 6 hours. The reaction mixture was cooled; the resulting crystal of 5-[4-[3-(5-methyl-2-phenyl-4-oxazolyl)propionyl]cinnamylidene]-2,4-oxazolidinedione was collected by filtration and washed with ether-methanol. The filtrate and washings were combined together and concentrated under reduced pressure; chloroform was added to the residue. The chloroform layer was washed by sequential additions of an aqueous solution of sodium hydrogen carbonate, 2N hydrochloric acid and water, dried (MgSO$_4$) and then concentrated; the residue was subjected to silica gel column chromatography. From the fraction eluted with ethyl acetate-hexane (2:1), further crop of 5-[4-[3-(5-methyl-2-phenyl-4-oxazolyl)propionyl]cinnamylidene]-2,4-oxazolidinedione was obtained. Combined crystals were recrystallized from dichloromethane-methanol to yield light yellow needles (1.12 g, 25%) having a melting point of 224°–225° C.

Reference Example 3

To a mixture of [(1,3-dioxolan-2-yl)methyl]triphenylphosphonium bromide (9.61 g) and N,N-dimethylformamide (DMF) (60 ml), sodium hydride (60% in oil, 0.9 g) was added, followed by stirring at room temperature for 20 minutes. To this mixture, 4-[3-(5-methyl-2-phenyl-4-oxazolyl)propionyl]benzaldehyde (6.50 g) was added, followed by stirring at room temperature for 4 hours. The reaction mixture was poured over ice water, neutralized with 2N HCl and then extracted with ethyl acetate. The ethyl acetate layer was washed with water, dried (MgSO$_4$) and then concentrated under reduced pressure; the residue was subjected to silica gel column chromatography. From the fraction eluted with ethyl acetate-chloroform (1:100), 4-[3-[4-[2-(1,3-dioxolan-2-yl)vinyl]phenyl]-3-oxopropyl]-5-methyl-2-phenyloxazole was obtained as an oily substance, which was then dissolved in tetrahydrofuran (THF) (150 ml). After addition of palladium-carbon (5%, 3.0 g), the solution was subjected to catalytic hydrogenation at 1 atm and room temperature. After the catalyst was filtered off, the filtrate was concentrated under reduced pressure; the residue was subjected to silica gel column chromatography. From the fraction eluted with ethyl acetate-hexane (1:3), 4-[3-[4-[2-(1,3-dioxolan-2-yl)ethyl]phenyl]-3-oxopropyl]-5-methyl-2phenyloxazole (2.4 g, 30%) was obtained, which was then recrystallized from ether-isopropyl ether to yield colorless needles having a melting point of 89°–90° C.

Reference Example 4

A mixture of 4-[3-[4-[2-(1,3-dioxolan- 2-yl)ethyl]phenyl]-3-oxopropyl]-5-methyl-2-phenyloxazole (2.17 g) and 50% acetic acid-water (60 ml) was stirred at 75°–80° C. for 4 hours. The reaction mixture was concentrated under reduced pressure, neutralized with an aqueous solution of sodium hydrogen carbonate and then extracted with ethyl acetate. The ethyl acetate layer was washed with water, dried (MgSO$_4$) and then concentrated under reduced pressure; the residue was subjected to silica gel column chromatography. From the fraction eluted with ether-hexane (1:1), 3-[4-[3-(5-methyl-2-phenyl-4-oxazolyl)propionyl]phenyl]propionaldehyde (1.5 g, 78%) was obtained, which was then recrystallized from ether-isopropyl ether to yield colorless needles having a melting point of 92°–93° C.

Reference Example 5

A mixture of 3-[4-[3-(5-methyl-2-phenyl-4-oxazolyl)propionyl]phenyl]propionaldehyde (1.47 g), sodium cyanide (0.25 g), acetic anhydride (0.52 g), benzyltributylammonium chloride [(C$_4$H$_9$)$_3$(C$_6$H$_5$CH$_2$)N$^+$Cl$^-$](0.66 g) and dichloromethane (30 ml)- water (10 ml) was stirred at room temperature for 18 hours. The organic layer was separated, washed with water, dried (MgSO$_4$) and then concentrated under reduced pressure. The residue was subjected to silica gel column chromatography. From the fraction eluted with ethyl acetate-hexane (1:2), 2-acetoxy-4-[4-[3-(5-methyl-2-phenyl-4-oxazolyl)propionyl]phenyl]butyronitrile (1.75 g, quantitative) was obtained as an oily substance. NMR (δ ppm in CDCl$_3$): 2.13 (3H, s), 2.15–2.3 (2H, m), 2.38 (3H, s), 2.8–3.0 (4H, m), 3.39 (2H, t, J=7 Hz), 5.29 (1H, t, J=6.5 Hz), 7.28 (2H, d, J=8 Hz), 7.35–7.5 (3H, m), 7.9–8.05 (4H, m)

Reference Example 6

A mixture of 2-acetoxy-4-[4-[3-(5-methyl-2-phenyl-4-oxazolyl)propionyl]phenyl]butyronitrile (1.72 g), 6 N HCl (20 ml) and dioxane (10 ml) was heated under refluxing conditions for 3 hours. The reaction mixture was poured over water and extracted with ethyl acetate. The ethyl acetate layer was washed with water, dried (MgSO$_4$) and then concentrated under reduced pressure to yield 2-hydroxy-4-[4-[3-(5-methyl-2-phenyl-4-oxazolyl) propionyl)phenyl]butyric acid as a solid substance. The solid was dissolved in ethanolic hydrogen chloride (10%, w/w, 20 ml), followed by stirring at 75°–80° C. for 2 hours. The reaction mixture was poured over water and extracted with ethyl acetate. The ethyl acetate layer was washed with water, dried (MgSO$_4$) and then concentrated under reduced pressure; the residue was subjected to silica gel column chromatography. From the fraction eluted with ethyl acetate-hexane (1:1), 2-hydroxy-4-[4-[3-(5-methyl-2-phenyl4-oxazolyl)propionyl] phenyl]butyric acid ethyl ester (1.54 g, 88%) was obtained, which was then recrystallized from dichloromethane-isopropyl ether to yield colorless needles having a melting point of 87°–88° C.

Reference Example 7

A mixture of 4-chloromethyl-5-methyl-2-(2-naphthyl)oxazole (10.0 g), triphenylphosphine (11.1 g) and acetonitrile (100 ml) was refluxed under heating conditions for 18 hours. After mixture cooling, the resulting crystal of [5-methyl-2-(2-naphthyl)-4-oxazolylmethyl]triphenylphosphonium chloride (19.3 g, 88%) was collected by filtration, which was then washed with acetonitrile and diethyl ether. Melting point 285°–286° C.
Elemental analysis (for C$_{33}$H$_{27}$NOPCl):
  Calculated: C, 76.22; H, 5.23; N, 2.69
  Found: C, 76.14; H, 5.50; N, 2.63

Reference Example 8

4-Chloromethyl-5-methyl-2-phenyloxazole and triphenylphosphine were reacted in the same manner as in Reference Example 7 to yield (5-methyl-2-phenyl-4-oxazolylmethyl)triphenylphosphonium chloride. Melting point 277°–278° C.
Elemental analysis (for C$_{29}$H$_{25}$NOPCl):
  Calculated: C, 74.12; H, 5.36; N, 2.98
  Found: C, 73.79; H, 5.32; N, 2.97

Reference Example 9

2-Chloromethyl-5-methyl-4-phenylthiazole and triphenylphosphine were reacted in the same manner as in Reference Example 7 to yield (5-methyl-4-phenyl-2-thiazolylmethyl)triphenylphosphonium chloride. Melting point 256°–257° C.
Elemental analysis (for $C_{29}H_{25}NPSCl$):
 Calculated: C, 71.67; H, 5.18; N, 2.88
 Found: C, 71.53; H, 5.15; N, 2.91

Reference Example 10

[5-Methyl-2-(2-naphthyl)-4-oxazolylmethyl]triphenylphosphonium chloride (18.4 g) was suspended in DMF (200 ml), and sodium hydride (60% in oil, 1.42 g) was added little by little at 0° C. After mixture stirring at room temperature for 1 hour, methyl 4-formylbenzoate (5.80 g) was added, followed by stirring for 3 hours. The reaction mixture was poured over ice-water; the resulting crystal was collected by filtration. The crystal was then purified by silica gel column chromatography to yield methyl (E)-4-[2-[5-methyl-2-(2-naphthyl)-4-oxazolyl]vinyl]benzoate (10.3 g, 79%) from the fraction eluted with ethyl acetate-chloroform (5:95, v/v), which was then recrystallized from dichloromethane-methanol to yield light yellow prisms having a melting point of 216°–217° C.

Reference Example 11

(5-Methyl-4-phenyl-2-thiazolylmethyl)triphenylphosphonium chloride and methyl 4-formylbenzoate were reacted in the same manner as in Reference Example 10 to yield methyl (E)-4-[2-(5-methyl-4-phenyl-2thiazolyl)vinyl]benzoate, which was then recrystallized from ethyl acetate to yield colorless plates having a melting point of 156°–157° C.

Reference Example 12

Methyl (E)-4-[2-[5-methyl-2-(2-naphthyl)-4-oxazolyl]vinyl]benzoate (9.30 g) was suspended in THF (250 ml), and lithium aluminum hydride (955 mg) was added little by little at 0° C. After mixture stirring at room temperature for 1 hour, water (5 ml) was added; the insoluble substances were filtered off. The filtrate was concentrated under reduced pressure; the resulting crystal was recrystallized from dichloromethane-methanol to yield (E)-4-[2-[5-methyl-2-(2-naphthyl)-4-oxazolyl]vinyl]benzyl alcohol (8.00 g, 93%) as colorless prisms having a melting point of 173°–174° C.

Reference Example 13

A mixture of methyl (E)-4-[2-(5-methyl-4-phenyl-2-thiazolyl)vinyl]benzoate (9.5 g), palladium-carbon (5%, 1.0 g) and dioxane (70 ml)-methanol (60 ml) was subjected to catalytic hydrogenation at 1 atm and room temperature. After the catalyst was filtered off, the filtrate was concentrated under reduced pressure to yield methyl 4-[2-(5-methyl-4-phenyl-2thiazolyl)ethyl]benzoate (9.0 g, 94%), which was then recrystallized from hexane to yield colorless plates having a melting point of 52°–53° C.

Reference Example 14

Methyl 4-[2-(5-methyl-4-phenyl-2-thiazolyl)ethyl]benzoate was reduced with lithium aluminum hydride in the same manner as in Reference Example 12 to yield 4-[2-(5-methyl-4-phenyl-2-thiazolyl)ethyl]benzyl alcohol, which was then recrystallized from ethyl acetate-hexane to yield colorless prisms having a melting point of 62°–63° C.

Reference Example 15

A mixture of (E)-4-[2-[5-methyl-2-(2-naphthyl)-4-oxazolyl]vinyl]benzyl alcohol (7.80 g), activated manganese dioxide (15.6 g) and chloroform (300 ml) was stirred at room temperature for 1 day. After the manganese dioxide was filtered off, the filtrate was concentrated under reduced pressure; the resulting crystal was recrystallized from dichloromethane-methanol to yield (E)-4-[2-[5-methyl-2-(2-naphthyl)-4-oxazolyl]vinyl]benzaldehyde (6.56 g, 85%) as light yellow needles having a melting point of 162°–163° C.

Reference Example 16

4-[2-(5-Methyl-4-phenyl-2-thiazolyl)ethyl]benzyl alcohol was oxidized with manganese dioxide in the same manner as in Reference Example 15 to yield 4-[2-(5-methyl-4-phenyl-2-thiazolyl)ethyl]benzaldehyde, which was then recrystallized from hexane to yield colorless prisms having a melting point of 66°–67° C.

Reference Example 17

(5-Methyl-2-phenyl-4-oxazolylmethyl)triphenylphosphonium chloride (25.4 g) was added to an ethanol solution of sodium ethoxide [prepared from sodium (1.4 g) and ethanol (300 ml)]under ice cooling conditions. After this reaction mixture was stirred at room temperature for 5 minutes, 4-bromobenzaldehyde (10.0 g) was added. After stirring at room temperature for 2 hours, the reaction mixture was poured over water and then extracted with ethyl acetate. The ethyl acetate layer was washed with water, dried (MgSO$_4$) and then concentrated under reduced pressure; the residue was subjected to silica gel chromatography to yield (E)-4-[2-(4bromophenyl)vinyl]-5-methyl-2-phenyl-4-oxazole (13.1 g, 71%) from the fraction eluted with ether-hexane (1:20, v/v), which was then recrystallized from ethyl acetate-hexane to yield colorless prisms having a melting point of 138°–139° C.

Reference Example 18

To a solution of (E)-4-[2-(4-bromophenyl)vinyl]-5-methyl-2-phenyl-4oxazole (13.0 g) in tetrahydrofuran (140 ml), a hexane solution of n-butyllithium (1.6 M, 28.7 ml) was added drop by drop at –70° C. After this reaction mixture was stirred at –70° C. for 15 minutes, a solution of N,N-dimethylformamide (4.2 g) in tetrahydrofuran (10 ml) was added drop by drop at the same temperature. The reaction mixture was stirred at –70° C. for 30 minutes and then the temperature was raised to room temperature, after which 1 N HCl (150 ml) was added drop by drop, followed by extraction with ethyl acetate. The ethyl acetate layer was washed with water, dried (MgSO$_4$) and then concentrated under reduced pressure; the residue was subjected to silica gel chromatography to yield (E)-4-[2-(5-methyl-2-phenyl-4-oxazolyl)vinyl]benzaldehyde (5.9 g, 54%) from the fraction eluted with ethyl acetate-hexane (1:2, v/v), which was then recrystallized from ethyl acetate-hexane to yield light brown prisms having a melting point of 158°–159° C.

Reference Example 19

To a mixture of (E)-4-[2-[5-methyl-2-(2-naphthyl)-4-oxazolyl]vinyl]benzaldehyde (4.00 g), triethyl phosphonoacetate (2.64 g) and N,N-dimethylformamide (70 ml), sodium hydride (60% in oil, 475 mg) was added little by little at 0° C. After stirring at room temperature for 2 hours, the reaction mixture was poured over ice water; the resulting crystal was collected by filtration. The crystal was then recrystallized from dichloromethane-ethanol to yield ethyl (E)-4-[2-[5-methyl-2-(2-naphthyl)-4-oxazolyl]vinyl]cinnamate (4.33 g, 90%) as light yellow prisms having a melting point of 186°–187° C.

Reference Example 20

(E)-4-[2-(5-Methyl-2-phenyl-4-oxazolyl)vinyl]benzaldehyde and triethyl phosphonoacetate were reacted in the same manner as in Reference Example 19 to yield ethyl (E)-4-[2-(5-methyl-2-phenyl-4-oxazolyl)vinyl]cinnamate, which was then recrystallized from ethyl acetate to yield light brown plates having a melting point of 161°–162° C.

Reference Example 21

4-[2-(5-Methyl-4-phenyl-2-thiazolyl)ethyl]benzaldehyde and triethyl phosphonoacetate were reacted in the same manner as in Reference Example 19 to yield ethyl 4-[2-(5-methyl-4-phenyl-2-thiazolyl)ethyl]cinnamate, which was then recrystallized from hexane to yield colorless prisms having a melting point of 69°–70° C.

Reference Example 22

A toluene solution of diisobutylaluminum hydride (1.5 M, 17 ml) was added drop by drop to a suspension of ethyl (E)-4-[2-[5-methyl-2-(2-naphthyl)4-oxazolyl]vinyl]cinnamate (4.20 g) in dichloromethane (100 ml) at 0° C. After the mixture was stirred at room temperature for 4 hours, methanol (2 ml) and then water (6 ml) were added at 0° C. After the insoluble substances were filtered off, the filtrate was concentrated under reduced pressure. The residue was subjected to silica gel chromatography to yield a crystal of (E,E)-3-[4-[2-[5-methyl-2-(2-naphthyl)-4-oxazolyl]vinyl]phenyl]-2-propenol from the fraction eluted with ethyl acetate-chloroform (5:95, v/v), which was then recrystallized from chloroform-ethanol to yield light yellow prisms (3.04 g, 81%) having a melting point of 184°–185° C.

Reference Example 23

Ethyl (E)-4-[2-(5-methyl-2-phenyl-4-oxazolyl)vinyl]cinnamate was reduced with diisobutylaluminum hydride in the same manner as in Reference Example 22 to yield (E,E)-3-[4-[2-(5-methyl-2-phenyl-4-oxazolyl)vinyl]phenyl]-2-propenol, which was then recrystallized from ethyl acetate to yield light yellow prisms having a melting point of 165°–166° C.

Reference Example 24

Ethyl 4-[2-(5-methyl-4-phenyl-2-thiazolyl)ethyl]cinnamate was reduced with diisobutylaluminum hydride in the same manner as in Reference Example 22 to yield (E)-3-[4-[2-(5-methyl-4-phenyl-2thiazolyl)ethyl]phenyl]-2-propenol, which was then recrystallized from hexane to yield colorless plates having a melting point of 93°–94° C.

Reference Example 25

A mixture of (E,E)-3-[4-[2-[5-methyl-2-(2-naphthyl)-4-oxazolyl]vinyl]phenyl]-2-propenol (2.80 g), activated manganese dioxide (8.40 g) and chloroform (150 ml) was stirred at room temperature for 16 hours. After the manganese dioxide was filtered off, the filtrate was concentrated under reduced pressure. The residue was subjected to silica gel chromatography to yield (E)-4-[2-[5-methyl-2-(2-naphthyl)-4-oxazolyl]vinyl]cinnamaldehyde (2.50 g, 90%) from the fraction eluted with chloroform, which was then recrystallized from dichloromethane-methanol to yield light yellow prisms having a melting point of 213°–214° C.

Reference Example 26

(E,E)-3-[4-[2-(5-Methyl-2-phenyl-4-oxazolyl)vinyl]phenyl]-2propenol was oxidized with activated manganese dioxide in the same manner as in Reference Example 25 to yield (E)-4-[2-(5-methyl-2-phenyl-4-oxazolyl)vinyl]cinnamaldehyde, which was then recrystallized from ethyl acetate to yield light yellow prisms having a melting point of 191°–192° C.

Reference Example 27

(E)-3-[4-[2-(5-Methyl-4-phenyl-2-thiazolyl)ethyl]phenyl]-2-propenol was oxidized with activated manganese dioxide in the same manner as in Reference Example 25 to yield 4-[2-(5-methyl-4-phenyl-2-thiazolyl)ethyl]cinnamaldehyde, which was then recrystallized from ethyl acetate-hexane to yield colorless prisms having a melting point of 94°–95° C.

Reference Example 28

A mixture of 4-[2-(5-methyl-4-phenyl-2-thiazolyl)ethyl] cinnamaldehyde (2.5 g), 2,4-oxazolidinedione (1.14 g), piperidine (0.211 g) and ethanol (50 ml) was refluxed under heating conditions for 4 hours. After the reaction mixture was concentrated, chloroform was added to the residue; the mixture was washed with 2 N HCl and water. The chloroform layer was washed with water, dried (MgSO$_4$) and then concentrated to yield 5-[4-[2-(5-methyl-4-phenyl-2-thiazolyl)ethyl]cinnamylidene]-2,4-oxazolidinedione[mixture of the (E)- and (Z)- configurations](0.81 g, 26%), which was then recrystallized from ethyl acetate to yield light yellow prisms having a melting point of 161°–162° C.

Reference Example 29

(E)-4-[2-(5-Methyl-2-phenyl-4-oxazolyl)vinyl]cinnamaldehyde and 2,4oxazolidinedione were reacted in the same manner as in Reference Example 28 to yield (E,E)-5-[4-[2-(5-methyl-2-phenyl-4-oxazolyl)vinyl]cinnamylidene]2,4-oxazolidinedione, which was then recrystallized from chloroform-methanol to yield yellow needles having a melting point of 274°–275° C.

Reference Example 30

4-Chloromethyl-2-(2-furyl)-5-methyloxazole and triphenylphosphine were reacted in the same manner as in Reference Example 7 to yield [2-(2-furyl)-5-methyl-4-oxazolylmethyl]triphenylphosphonium chloride. Melting point 284°–285° C.

Elemental analysis (for $C_{27}H_{23}NO_2PCl$):

Calculated: C, 70.51; H, 5.04; N, 3.05

Found: C, 70.25; H, 4.97; N, 3.09

Reference Example 31

(5-Methyl-2-phenyl-4-oxazolylmethyl)triphenylphosphonium chloride and methyl 4-formylbenzoate were reacted in the same manner as in Reference Example 10 to yield methyl (E)-4-[2-(5-methyl-2-phenyl-4-oxazolyl)vinyl]benzoate, which was then recrystallized from ethyl acetate to yield colorless prisms having a melting point of 164°–165° C.

Reference Example 32

Methyl (E)-4-[2-(5-methyl-2-phenyl-4-oxazolyl)vinyl]benzoate was subjected to catalytic hydrogenation in the same manner as in Reference Example 13 to yield methyl 4-[2-(5-methyl-2-phenyl-4-oxazolyl)ethyl]benzoate, which was then recrystallized from hexane to yield colorless needles having a melting point of 59°–60° C.

Reference Example 33

Methyl 4-[2-(5-methyl-2-phenyl-4-oxazolyl)ethyl]benzoate was reduced with lithium aluminum hydride in the same manner as in Reference Example 12 to yield 4-[2-(5-methyl-2-phenyl-4-oxazolyl)ethyl]benzyl alcohol, which was then recrystallized from ethyl acetate-hexane to yield colorless plates having a melting point of 103°–104° C.

Reference Example 34

A mixture of 4-[2-(5-methyl-2-phenyl-4-oxazolyl)ethyl] benzyl alcohol (11.3 g), activated manganese dioxide (23.0 g) and dichloromethane (200 ml) was stirred at room temperature for 3 hours. After the manganese dioxide was filtered off, the filtrate was concentrated under reduced pressure. The residual crystal and triethyl phosphonoacetate (7.5 g) were dissolved in tetrahydrofuran (THF) (150 ml), and sodium hydride (60% in oil, 1.6 g) was added little by little under ice cooling conditions. After stirring at room temperature for 1 hour, the reaction mixture was poured over water and extracted with ethyl acetate. The ethyl acetate layer was washed with water, dried ($MgSO_4$), and then concentrated under reduced pressure, to yield ethyl 4-[2-(5-methyl-2-phenyl-4-oxazolyl)ethyl]cinnamate (7.9 g, 57%), which was then recrystallized from ethyl acetate-hexane to yield colorless prisms having a melting point of 73°–74° C.

Reference Example 35

Ethyl 4-[2-(5-methyl-2-phenyl-4-oxazolyl)ethyl]cinnamate was reduced with diisobutylaluminum hydride in the same manner as in Reference Example 22 to yield (E)-3-[4-[2-(5-methyl-2-phenyl-4-oxazolyl)ethyl]phenyl]2-propenol, which was then recrystallized from ethyl acetate-hexane to yield colorless needles having a melting point of 102°–103° C.

Reference Example 36

(E)-3-[4-[2-(5-Methyl-2-phenyl-4-oxazolyl)ethyl]phenyl]-2-propenol was oxidized with activated manganese dioxide in the same manner as in Reference Example 25 to yield 4-[2-(5-methyl-2-phenyl-4-oxazolyl)ethyl]cinnamaldehyde, which was then recrystallized from ethyl acetate-hexane to yield colorless prisms having a melting point of 99°–100° C.

Reference Example 37

4-[2-(5-Methyl-2-phenyl-4-oxazolyl)ethyl]cinnamaldehyde and triethyl phosphonoacetate were reacted in the same manner as in Reference Example 19 to yield ethyl (E,E)-5-[4-[2-(5-methyl-2-phenyl-4-oxazolyl)ethyl]phenyl]2,4-pentadienoate, which was then recrystallized from ethyl acetate-hexane to yield colorless prisms having a melting point of 82°–83° C.

Reference Example 38

Ethyl (E,E)-5-[4-[2-(5-methyl-2-phenyl-4-oxazolyl)ethyl]phenyl]-2,4pentadienoate was reduced with diisobutylaluminum hydride in the same manner as in Reference Example 22 to yield (E,E)-5-[4-[2-(5-methyl-2-phenyl4-oxazolyl)ethyl]phenyl]-2,4-pentadien-1-ol, which was then recrystallized from ethyl acetate-hexane to yield colorless prisms having a melting point of 117°–118° C.

Reference Example 39

(E,E)-5-[4-[2-(5-methyl- 2-phenyl-4-oxazolyl )ethyl]phenyl ]- 2,4-pentadien-1-ol was oxidized with activated manganese dioxide in the same manner as in Reference Example 25 to yield (E,E)-5-[4-[2-(5-methyl-2-phenyl4-oxazolyl)ethyl]phenyl]-2,4-pentadien-1-al, which was then recrystallized from ethyl acetate to yield yellow rods having a melting point of 107°–108° C.

Reference Example 40

[2-(2-Furyl)-5-methyl-4-oxazolylmethyl]triphenylphosphonium chloride and methyl 4-formylbenzoate were reacted in the same manner as in Reference Example 10 to yield methyl (E)-4-[2-[2-(2-furyl)-5-methyl-4-oxazolyl]vinyl]benzoate, which was then recrystallized from ethyl acetate to yield colorless prisms having a melting point of 142°–143° C.

Reference Example 41

Methyl (E)-4-[2-[2-(2-furyl)-5-methyl-4-oxazolyl]vinyl]benzoate was reduced with lithium aluminum hydride in the same manner as in Reference Example 12 to yield (E)-4-[2-[2-(2-furyl)-5-methyl-4-oxazolyl]vinyl]benzyl alcohol, which was then recrystallized from ethyl acetate-hexane to yield colorless prisms having a melting point of 150°–15° C.

Reference Example 42

(E)-4-[2-[2-(2-Furyl)-5-methyl-4-oxazolyl]vinyl]benzyl alcohol was oxidized with activated manganese dioxide in the same manner as in Reference Example 25 to yield (E)-4-[2-[2-(2-furyl)-5-methyl-4-oxazolyl]vinyl]benzaldehyde, which was then recrystallized from ethyl acetate to yield colorless prisms having a melting point of 209°–210° C.

Reference Example 43

(E)-4-[2-[2-(2-Furyl)-5-methyl-4-oxazolyl]vinyl]benzaldehyde and triethyl phosphonoacetate were reacted in the same manner as in Reference Example 19 to yield ethyl (E)-4-[2-[2-(2-furyl)-5-methyl-4-oxazolyl]vinyl]cinnamate, which was then recrystallized from ethanol to yield light yellow prisms having a melting point of 123°–124° C.

Reference Example 44

Ethyl (E)-4-[2-[2-(2-furyl)-5-methyl-4-oxazolyl]vinyl]cinnamate was reduced with diisobutylaluminum hydride in the same manner as in Reference Example 22 to yield (E,E)-4-[2-[2-(2-furyl)-5-methyl-4-oxazolyl]vinyl]phenyl]-2-propenol, which was then recrystallized from ethyl acetate to yield colorless prisms having a melting point of 148°–149° C.

Reference Example 45

(E,E)-4-[2-[2-(2-Furyl)-5-methyl-4-oxazolyl]vinyl]phenyl]-2-propenol was oxidized with activated manganese dioxide in the same manner as in Reference Example 25 to yield (E)-4-[2-[2-(2-furyl)-5-methyl-4-oxazolyl]vinyl]phenyl]cinnamaldehyde, which was then recrystallized from ethyl acetate-hexane to yield light yellow prisms having a melting point of 199°–200° C.

Reference Example 46

(E)-4-[2-[2-(2-Furyl)-5-methyl-4-oxazolyl]vinyl]phenyl]cinnamaldehyde and triethyl phosphonoacetate were reacted in the same manner as in Reference Example 19 to yield ethyl (E,E,E)-5-[4-[2-[2-(2-furyl)-5-methyl-4oxazoly]vinyl]phenyl]-2,4-pentadienoate, which was then recrystallized from ethanol to yield light brown prisms having a melting point of 155°–156° C.

Reference Example 47

Ethyl (E,E,E)-5-[4-[2-[2-(2-furyl)-5-methyl-4-oxazolyl]vinyl]phenyl]2,4-pentadienoate was reduced with diisobutylaluminum hydride in the same manner as in Reference Example 22 to yield (E,E,E)-5-[4-[2-[2-(2-furyl)-5-methyl-4-oxazolyl]vinyl]phenyl]-2,4-pentadien-1-ol, which was then recrystallized from ethyl acetate to yield colorless needles having a melting point of198°–199° C.

Reference Example 48

(E,E,E)-5-[4-[2-[2-(2-Furyl)-5-methyl-4-oxazolyl]vinyl]phenyl]-2,4-pentadien-1-ol was oxidized with activated manganese dioxide in the same manner as in Reference Example 25 to yield (E,E,E)-5-[4-[2-[2-(2-furyl)-5- methyl-4-oxazolyl]vinyl]phenyl]-2,4-pentadien-1-al, which was then recrystallized from ethyl acetate to yield light brown prisms having a melting point of 179°–180° C.

Reference Example 49

A mixture of (E,E,E)-5-[4-[2-[2-(2-furyl)-5-methyl-4-oxazolyl]vinyl]phenyl]-2,4-pentadien-1-al (2.4 g), palladium-carbon (5%, 0.3 g) and ethyl acetate (100 ml) was subjected to catalytic hydrogenation at 1 atm and room temperature. After the catalyst was filtered off, the filtrate was concentrated under reduced pressure. The residue was subjected to silica gel chromatography to yield 5-[4-[2-[2-(2-furyl)-5-methyl-4-oxazolyl]ethyl]phenyl]pentan-1-al (2.2 g, 92%) as an oily substance from the fraction eluted with ethyl acetate-hexane (1:1, v/v).
NMR (δ ppm in CDCl$_3$):

1.6–1.7 (4H, m), 2.05 (3H, s), 2.4–2.5 (2H, m), 2.55–2.65 (2H, m), 2.7–2.8 (2H, m), 2.9–3.0 (2H, m), 6.52 (1H, dd, J=3.5 & 1.8 Hz), 6.93 (1H, d, J=3.5 Hz) 7.07 (4H, s), 7.53 (1H, d, J =1.8 Hz), 9.76 (1H, t, J =1.8 Hz)

Reference Example 50

After a mixture of 5-[4-[2-[2-(2-furyl)-5-methyl-4-oxazolyl]ethyl]phenyl]pentan-1-al (2.2 g), sodium cyanide (0.383 g), acetic anhydride (0.796 g), benzyltributylammonium chloride (0.608 g) and dichloromethane (40 ml)water (10 ml) was stirred at room temperature for 2 hours, the organic layer was separated, washed with water, dried (MgSO$_4$), and then concentrated under reduced pressure, to yield 2-acetoxy-6-[4-[2-[2-(2-furyl)-5-methyl-4-oxazolyl]ethyl]phenyl]hexanenitrile as an oily substance.
NMR (δ ppm in CDCl$_3$):

1.6–1.8 (6H, m), 2.06 (3H, s), 2.13 (3H, s), 2.61 (2H, t, J=6.8 Hz), 2.7–2.8 (2H, m), 2.9–3.0 (2H, m), 5.31 (1H, t, J=6.8 Hz), 6.52 (1H, dd, J=3.5 & 1.8 Hz), 6.93 (1H, d, J=3.5Hz), 7.08 (4H, s), 7.53 (1H, d, J=1.8 Hz)

To this oily substance, 6 N HCl (50 ml) was added, followed by heating under refluxing conditions for 8 hours. After cooling, the reaction mixture was poured over water and extracted with ethyl acetate. The ethyl acetate layer was washed with water, dried (MgSO$_4$), and then concentrated under reduced pressure, to yield 2-hydroxy-6-[4-[2-[2-(2-furyl)-5-methyl-4-oxazolyl]ethyl]phenyl]hexanoic acid as an oily substance.

This 2-hydroxy-6-[4-[2-[2-(2-furyl)-5-methyl-4-oxazolyl]ethyl]phenyl]hexanoic acid was dissolved in ethanol (40 ml). To this solution, concentrated sulfuric acid (3 drops) was added, followed by heating under refluxing conditions for 16 hours, after which the reaction mixture was poured over water and extracted with ethyl acetate. The ethyl acetate layer was washed with water, dried (MgSO$_4$), and then concentrated under reduced pressure; the residue was subjected to silica gel chromatography to yield ethyl 2-hydroxy-6-[4-[2-[2-(2-furyl)-5-methyl-4-oxazolyl]ethyl]hexanoate (1.9 g, 70%) as an oily substance from the fraction eluted with chloroform-ethyl acetate (5:1, v/v).
NMR (δ ppm in CDCl$_3$):

1.28 (3H, t, J =7 Hz), 1.4–1.9 (6H, m), 2.05 (3H, s), 2.58 (2H, t, J =6.8 Hz), 2.65–2.80 (2H, m), 2.85–2.95 (2H, m), 4.1–4.2 (1H, m), 4.23 (2H, q, J=7 Hz), 6.51 (1H, dd, J=3.6 & 2.0 Hz), 6.91 (1H, d, J=3.6 Hz), 7.06 (4H, s), 7.52 (1H, d, J=2.0 Hz)

Reference Example 51

A mixture of (E,E)-5-[4-[2-(5-methyl-2-phenyl-4-oxazolyl)ethyl]phenyl]-2,4-pentadien-1-al (2.3 g), 2,4-oxazolidinedione (2.0 g), piperidine (0.596 g) and acetic acid (50 ml) was refluxed under heating conditions for 15 hours. The reaction mixture was concentrated; water was added to the residue, followed by acidification with 2N HCl and subsequent extraction with ethyl acetate. The ethyl acetate layer was washed with water, dried (MgSO$_4$), and then concentrated. The residue was subjected to silica gel chromatography to yield 5-[(E,E)-5-[4-[2-(5-methyl-2-phenyl-4-oxazolyl)ethyl]phenyl]-2,4pentadienylidene]-2,4-oxazolidinedione [mixture of the (E)- and (Z)- configurations](1.0 g, 33%) from the fraction eluted with chloroform-ethyl acetate (9:1, v/v), which was then recrystallized from chloroform-methanol to yield light yellow prisms having a melting point of 208°–210° C.

Reference Example 52

(E)-4-[2-[2-(2-Furyl)-5-methyl-4-oxazolyl]vinyl]phenyl]cinnamaldehyde and 2,4-oxazolidinedione were reacted in the same manner as in Reference Example 51 to yield 5-[4-[(E)-2-[2-(2-furyl)-5-methyl-4-oxazolyl]vinyl]cinnamylidene]-2,4-oxazolidinedione [mixture of the (E)- and (Z)-configurations], which was then recrystallized from chloroform-methanol to yield a light brown prism having a melting point of 290°–291° C.

We claim:
1. A 2,4-oxaozolidinedione compound of the formula

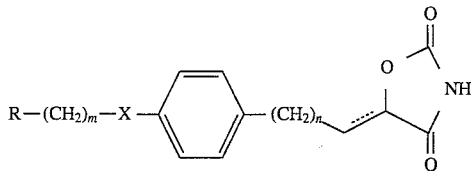

wherein
X represents —CH$_2$—, or —CH=CH—,
R is 2-oxazolyl, 4-oxazolyl or 5-oxazolyl each of which may have 1 or 2 substituents at any possible position on the ring thereof, selected from the group consisting of
(1) aliphatic chain hydrocarbon selected from the group consisting of alkyl groups having 1 to 10 carbon atoms, alkenyl groups having 2 to 10 carbon atoms and alkynyl groups having up to 6 carbon atoms;
(2) alicyclic hydrocarbon selected from the group consisting of cycloalkyl having up to 10 carbon atoms, cycloalkenyl having up to 6 carbon atoms and cycloalkadienyl having up to 6 carbon atoms;
(3) aryl selected from the group consisting of phenyl, naphthyl, anthryl, phenanthryl and acenaphthylenyl;
(4) aromatic heterocyclic selected from the group consisting of furyl, thienyl, pyrrolyl,-oxazolyl, isoxazolyl, imidazolyl, pyrazolyl, 1,2,3-triazolyl, 1,2,4-triazolyl, tetrazolyl, pyradinyl, benzofuranyl, isobenzofuranyl, benzo [b]thienyl, indolyl, isoindolyl, 1H-indazolyl, benzimidazolyl, benzoxazolyl, 1,2-benzisoxazolyl, 1H-benzotriazolyl, carbazolyl, phenoxthinyl and thianthrenyl;
(5) non-aromatic heterocyclic selected from the group consisting of oxilanyl, azetidinyl, oxetanyl, thietanyl, pyrrolidinyl, tetrahydrofuryl, thiolanyl and tetrahydropyranyl;
(6) halogen;
(7) nitro;
(8) hydroxyl;
(9) alkoxy having 1 to 10 carbon atoms;
(10) alkenyloxy having 2 to 10 carbon atoms;
(11) phenyl-C$_{1-4}$ alkyloxy;
(12) alkanoyloxy having 2 to 4 carbon atoms;
(13) aryloxy selected from the group consisting of phenoxy and 4-chlorophenoxy;
(14) thiol;
(15) alkylthio having 1 to 10 carbon atoms;
(16) phenyl-C$_{1-4}$, alkylthio;
(17) alkanoylthio having 2 to 4 carbon atoms;
(18) amino which may have 1 to 2 substituents selected from the group consisting of alkyl having 1 to 10 carbon atoms, alkenyl having 2 to 10 carbon atoms, phenyl and carboxylic acyl having 2 to 10 carbon atoms;
(19) acyl selected from the group consisting of formyl, C$_{1-10}$ alkylcarbonyl, C$_{2-10}$ alkenyl-carbonyl and aromatic-carbonyl selected from the group consisting of benzoyl and nicotinoyl,
(20) carboxyl; and
(21) esterified carboxyl selected from the group consisting of alkoxycarbonyl having 2 to 5 carbon atoms, benzyloxycarbonyl and aryloxycarbonyl selected from the group consisting of phenoxycarbonyl and p-tolyloxycarbonyl;

each of the above substituents (2), (3) and (4) may be substituted by 1 to 3 substituents selected from the group consisting of
1) lower alkyl;
2) lower alkenyl;
3) lower alkynyl;
4) cycloalkyl having up to 10 carbon atoms;
5) aryl selected from the group consisting of phenyl, naphthyl, anthryl, phenanthryl and acenaphthylenyl;
6) aromatic heterocyclic selected from the group consisting of furyl, thienyl, pyrrolyl,-oxazolyl, isoxazolyl, imidazolyl, pyrazolyl, 1,2,3-triazolyl, 1,2,4-triazolyl, tetrazolyl, pyradinyl, benzofuranyl, isobenzofuranyl, benzo-[b]thienyl, indolyl, isoindolyl, 1H-indazolyl, benzimidazolyl, benzoxazolyl, 1,2-benzisoxazolyl, 1H-benzotriazolyl, carbazolyl, phenoxthinyl and thianthrenyl;
7) non-aromatic heterocyclic selected from the group consisting of oxilanyl, azetidinyl, oxetanyl, thietanyl, pyrrolidinyl, tetrahydrofuryl, thiolanyl and tetrahydropyranyl;
8) phenyl- C$_{1-4}$ alkyl;
9) amino which may have 1 to 2 substituents selected from the group consisting of alkyl having 1 to 10 carbon atoms, alkenyl having 2 to 10 carbon atoms, phenyl and carboxylic acyl having 2 to 10 carbon atoms;
10) amidino;
11) acyl selected from the group consisting of formyl, C$_{1-10}$ alkylcarbonyl, C$_{2-10}$ alkenyl-carbonyl and aromatic-carbonyl selected from the group consisting of benzoyl and nicotinoyl;
12) carbamoyl which may have 1 to 2 substituents selected from the group consisting of alkyl having 1 to 10 carbon atoms, alkenyl having 2 to 10 carbon atoms, phenyl and carboxylic acyl having 2 to 10 carbon atoms,
13) sulfamoyl which may have 1 to 2 substituents selected from the group consisting of alkyl having 1 to 10 carbon atoms, alkenyl having 2 to 10 carbon atoms, phenyl and carboxylic acid having 2 to 10 carbon atoms;
14) carboxyl;
15) alkoxycarbonyl having 2 to 5 carbon atoms;
16) hydroxyl;
17) alkoxy having 1 to 10 carbon atoms;
18) alkenyloxy having 2 to 10 carbon atoms;
19) cycloalkyloxy selected from the group consisting of cyclobutoxy, cyclopentyloxy and cyclohexyloxy;
20) phenyl-C$_{1-4}$ alkyloxy;
21) aryloxy selected from the group consisting of phenoxy and 4chlorophenoxy;
22) mercapto;
23) alkylthio having 1 to 10 carbon atoms;
24) phenyl-C$_{1-4}$ alkylthio;
25) arylthio;
26) sulfo;
27) cyano;
28) azide;
29) nitro;
30) nitroso; and
31) halogen;

n represents an integer of from 1 to 5,
m represents an integer of from 1 to 3, and
....... represents a single bond or a double bond, or a pharmaceutically acceptable salt thereof.

2. A compound as claimed in claim 1, wherein m is 2 and n is 1 or 2.

3. A compound as claimed in claim 1, wherein m is 1 and n is 2.

4. A compound as claimed in claim 1, wherein x is —CH=CH—.

5. A compound as claimed in claim 1, wherein the compound is 5-[3[-4-[3-(5-methyl-2-phenyl-4-oxazolyl)-1-propenyl]phenyl]propyl]-2,4-oxazalidinedione.

6. The compound 5-[4 as claimed in claim 1, wherein the compound is 5-[4-[3-(5-methyl-2-phenyl-4-oxazolyl)-1-propenyl ]benzyl ]-2,4-oxazolidinedione.

7. A compound as claimed in claim 1, wherein the compound is 5-[3-[4-[2-[5-methyl-2-(2-naphthyl)-4-oxazolyl]ethyl]phenyl]propyl]-2,4-oxazolidinedione.

8. A compound as claimed in claim 1, wherein the compound is 5-[3[-4-[2-(5-methyl-2-phenyl-4-oxazolyl)ethyl]phenyl]propyl]-2,4-oxazolidinedione.

9. A pharmaceutical composition for treating diabetes mellitus or hyperlipemia which comprises an effective amount of a compound or pharmaceutically acceptable salt thereof as defined in claim 1 and a pharmaceutically acceptable carrier therefor.

10. A method for treating a mammal suffering from diabetes mellitus or hyperlipemia Which comprises administering to said mammal an effective amount of a compound or pharmaceutically acceptable salt thereof as defined in claim 1.

* * * * *